US006271444B1

(12) United States Patent
McBride et al.

(10) Patent No.: US 6,271,444 B1
(45) Date of Patent: Aug. 7, 2001

(54) ENHANCER ELEMENTS FOR INCREASED TRANSLATION IN PLANT PLASTIDS

(75) Inventors: Kevin E. McBride, Davis, CA (US); Jeffrey M. Staub, Chesterfield, MO (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 09/113,690

(22) Filed: Jul. 10, 1998

(51) Int. Cl.[7] .............................. C12N 5/04; C12N 15/29; C12N 15/31; C12N 15/33; C12N 15/82
(52) U.S. Cl. ........................ 800/300; 800/278; 800/287; 800/288; 435/69.1; 435/418; 435/419; 435/468; 536/23.2; 536/23.6; 536/23.7; 536/23.72; 536/24.1
(58) Field of Search ..................... 536/23.2, 23.6, 536/23.7, 24.1, 23.72; 435/69.1, 418, 419, 468; 800/278, 287, 288, 300

(56) References Cited

U.S. PATENT DOCUMENTS

| 5,015,580 | 5/1991 | Christou et al. ................... 435/172.3 |
| 5,232,840 | 8/1993 | Olins et al. ......................... 435/69.1 |
| 5,378,619 | 1/1995 | Roger ................................. 435/172.3 |
| 5,416,011 | 5/1995 | Hinchee et al. ................... 435/172.3 |
| 5,424,199 | 6/1995 | Goeddel et al. ..................... 435/69.4 |
| 5,576,198 | 11/1996 | McBride et al. ..................... 435/91.3 |
| 5,693,507 | * 12/1997 | Daniel et al. ...................... 435/172.3 |
| 5,877,402 | * 3/1999 | Maliga et al. ......................... 800/205 |

FOREIGN PATENT DOCUMENTS

| 0241446B1 | 1/1995 | (EP) . |
| 2183660A | 6/1987 | (GB) . |
| WO 92/15675 | 9/1992 | (WO) . |

OTHER PUBLICATIONS

Fargo et al. Mol. Gen. Genet. 257(3): 271–282, 1998.*
Zhou et al. Plant Cell Reports 15: 159–163, 1995.*
Daniell et al. Nature Biotechnology 16: 345–348, 1998.*
Horsch, et al., "A simple and general method for transferring genes into plants" *Science* 227, 1229–1231 (1985).
Klein, et al., "Transformation of microbes, plants and animals by particle bombardment" *Bio/Technology* 10, 286–291 (1992).
Shinozaki, et al., "The complete nucleotide sequence of the tobacco chloroplast genome: its gene organization and expression" *The EMBO Journal* 5(9), 2043–2049 (1986).
Zoubenko, et al., "Efficient targeting of foreign genes into the tobacco plastid genome" *Nucleic Acids Research* 22(19), 3819–3824 (1994).
Sanford, et al., "Optimizing the biolistic process for different biological applications" *Methods in Enzymology* 217, 483–509 (1993).
Ye, et al., "Optimization of delivery of foreign DNA into higher–plant chloroplasts" *Plant Molecular Biology* 15, 809–819 (1990).

Blowers, et al., "Studies on Chlamydomonas chloroplast transformation: Foreign DNA can be stably maintained in the chromosome" *The Plant Cell* 1, 123–132 (1989).
McBride, et al., "Controlled expression to plastid transgenes in plants based on a nuclear DNA–encoded and plastid–targeted T7 RNA polymerase" *Proceedings of the National Academy of Sciences of the USA* 91, 7301–7305 (1994).
Daniell, et al., "Foreign gene expression in chloroplasts of higher plants mediated by tungsten particle bombardment" *Methods in Enzymology* 217, 536–557 (1993).
Svab, et al., "High–frequency plastid transformation in tobacco by selection for a chimeric aad A gene" *Proceedings of the National Academy of Sciences of the USA* 90, 913–917 (1993).
Svab, et al., "Stable transformation of plastids in higher plants" *Proceedings of the National Academy of Sciences of the USA* 87, 8526–8530 (1990).
Staub, et al., "Accumulation of D1 polypeptide in tobacco plastids is regulated via the untranslated region of the psbA mRNA" *The EMBO Journal* 12(2), 601–606 (1993).
Daniell, et al., "Uptake and expression of bacterial and cyanobacterial genes by isolated cucumber etioplasts" *Proceedings of the National Academy of Sciences of the USA* 84, 6349–6353 (1987).
Herrera–Estrella, et al., "Expression of chimaeric genes transfered into plant cells using a Ti–plasmid–derived vector" *Nature* 303, 209–213 (1983).
De Block, et al., "Chloroplast transformation by *Agrobacterium tumefaciens*" *The EMBO Journal* 4(6), 1367–1372 (1985).
Herrera–Estralla, et al., "Light–inducible and chloroplast–associated expression of a chimaeric gene introduced into Nicotianatabacum using a Ti plasmid vector" *Nature* 310, 115–120 (1984).
Maliga, et al., "Towards plastic transformation in flowering plants" *Tibtech* 11, 101–107 (1993).
Boynton, et al., "Chloroplast transformation in Chlamydomonas with high velocity microprojectiles" *Science* 240, 1534–1538 (1988).
Olins, et al., "The T7 phage gene 10 leader RNA, a ribosome–binding site that dramatically enhances the expression of foreign genes in *Escherichia coli*" *Gene* 73, 227–235 (1988).

(List continued on next page.)

*Primary Examiner*—David T. Fox
(74) *Attorney, Agent, or Firm*—Calgene LLC

(57) ABSTRACT

Provided are methods for increasing the production of protein in a plant cell by transforming plastids of plant cells with a construct comprising a promoter functional in a plant plastid, a ribosome binding site, DNA sequence of interest and a transcription termination region, and growing plant cells comprising the transformed plastids under conditions wherein the DNA encoding sequence is transcribed in the plastid. Also provided are methods for increasing protein production by fusing a coding sequence to a gene of interest to a secondary protein for cleavage or targetting of the protein of interest within the plastid, whereby high levels of expression of protein is achieved.

12 Claims, 15 Drawing Sheets

OTHER PUBLICATIONS

Konishi, et al., "Transit peptides of thylakoid luminal proteins: the sites of stromal processing are conserved amonghigher plants" *Plant Cell Physiology* 34(7), 1081–1087 (1993).

Bassham, et al., "Transport of proteins into chloroplasts" *The Journal of Biological Chemistry* 266(35), 23606–23610 (1991).

Bilang, et al., "Containing excitement over transplastomic plants" *Nature Biotechnology* 16, 333–334 (1998).

Sprengart, et al., "The initiation of translation in *E. coli*: apparent base pairing between the 16srRNA and downstream sequences of the mRNA" *Nucleic Acids Research* 18(7), 1719–1723 (1990).

Bonham–Smith, et al., "Translation of chloroplast–encoded mRNA: potential initiation and termination signals" *Nucleic Acids Research* 17(5), 2057–2080 (1989).

McBride, et al., "Amplification of a chimeric Bacillus gene in chloroplasts leads to an extraordinary level of an insecticidal protein in tobacco" *Bio/Technology* 13, 362–365 (1995).

Staub, et al., "Expression of a chimeric uidA gene indicates that polycistronic mRNAs are efficiently translated in tobacco plastids" *The Plant Journal* 7(5), 845–848 (1995).

Leung, et al., "Growth hormone receptor and serum binding protein: purification, cloning and expression" *Nature* 330, 537–543 (1987).

Nicoll, et al., "Structural features of prolactins and growth hormones that can be related to their biological properties" *Endocrine Reviews* 7(2), 169–203 (1986).

* cited by examiner

5'- AAT TGT AGA AAT AAT TTT GTT TAA CTT TAA GAA GGA GAT ATA CC-3'
    TTA ACA TCT TTA TTA AAA CAA ATT GAA ATT CTT CCT CTA TAT GG

FIGURE 1

SEQUENCE RANGE: 1 TO 5004

| ENZYME | # CUTS | POSITIONS | | | |
|---|---|---|---|---|---|
| BamHI | 1 | 295 | | | |
| BglII | 2 | 238 | 2074 | | |
| BsaI | 2 | 272 | 4136 | | |
| BspHI | 2 | 3411 | 4910 | | |
| DraI | 3 | 1415 | 3902 | 4652 | |
| EcoRI | 3 | 275 | 869 | 1272 | |
| EcoRV | 1 | 289 | | | |
| HindIII | 2 | 301 | 2239 | | |
| KpnI | 1 | 2537 | | | |
| MluI | 1 | 2125 | | | |
| NcoI | 1 | 1657 | | | |
| PstI | 3 | 285 | 311 | 1801 | |
| PvuI | 2 | 84 | 4445 | | |
| PvuII | 4 | 113 | 541 | 1078 | 1730 |
| SacI | 3 | 749 | 1715 | 2530 | |
| SalI | 1 | 2507 | | | |
| ScaI | 1 | 4555 | | | |
| SpeI | 2 | 1964 | 2540 | | |
| SphI | 1 | 1652 | | | |
| SspI | 5 | 1353 | 1411 | 3885 | 3906 | 4879 |
| XbaI | 1 | 2513 | | | |
| XhoI | 3 | 269 | 319 | 1881 | |

ApaI
ApaI*
AscI
BclI*
BlpI
BsrGI
ClaI
ClaI*
NotI
PacI
SacII
SfiI
SfiI*
SmaI
XbaI*

FIG.6B

Peak I (tallest peak) has the retention time expected for properly folded, native 22 kDa GP2000. This peak was collected and dried down in a Savant Speed-Vac for amino terminal sequencing and electrospray mass spectrometry.

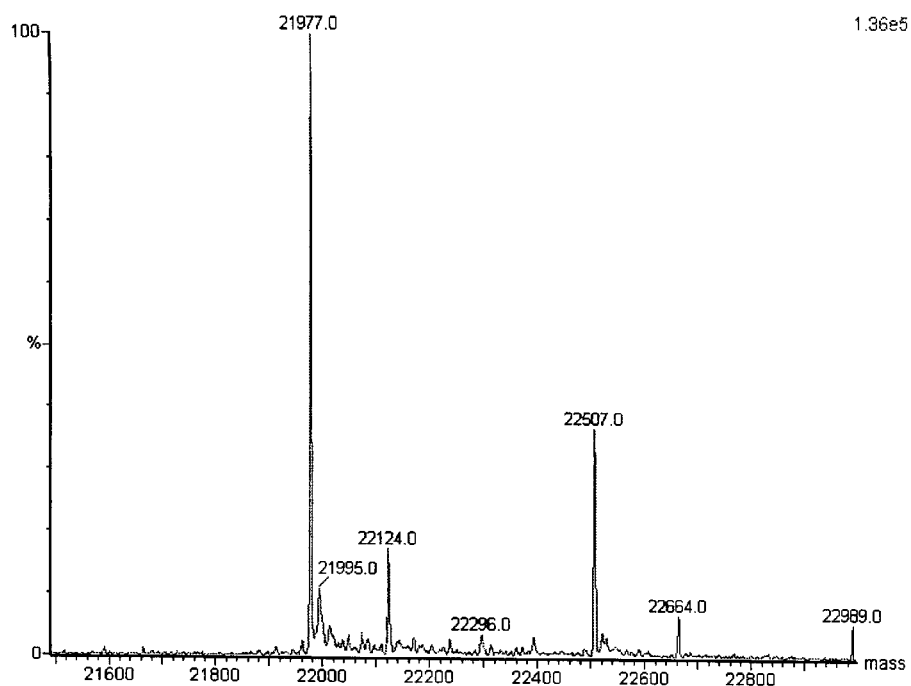

Mass spectrometry of RP-HPLC peak I shown above. Note that there are 4 major protein species, of different molecular mass.

21977 kDa  -  This is the predicted mass of "des-Phe"-GP2000, ie. GP2000 with the predicted N-terminal Phe removed by over-cleavage of Ubiquitin protease.

****22124 kDa  -  This is the predicted mass of properly processed, correct amino acid sequence GP2000

22507 kDa  -  This is probably des-Phe-GP2000 modified during plant extraction procedures 22664 kDa  -  This is probably GP2000 modified during plant extraction procedures Amino terminal sequencing was done by standard Edman degradation, and confirmed the N-terminal sequences discussed above.

Figure 12

```
                        SEQUENCE LISTING

<160> NUMBER OF SEQ ID NOS: 3

<210> SEQ ID NO 1
<211> LENGTH: 88
<212> TYPE: DNA
<213> ORGANISM: Artificial Sequence
<220> FEATURE:
<223> OTHER INFORMATION: G10L ribosome binding site

<400> SEQUENCE: 1
aattgtagaa ataattttgt ttaactttaa gaaggagata taccttaaca tctttattaa    60
aacaaattga aattcttcct ctatatgg                                       88

<210> SEQ ID NO 2
<211> LENGTH: 58
<212> TYPE: PRT
<213> ORGANISM: Aprotinin

<400> SEQUENCE: 2

Arg Pro Asp Phe Cys Leu Glu Pro Pro Tyr Thr Gly Pro Cys Lys Ala
 1               5                  10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 3
<211> LENGTH: 44
<212> TYPE: DNA
<213> ORGANISM: Artificial Sequence
```

-continued

```
<220> FEATURE:
<223> OTHER INFORMATION: Synthetic Oligonucleotide

<400> SEQUENCE: 3
catgggtata tctccttctt aaagttaaac aaaattattt ctac                    44
```

ENHANCER ELEMENTS FOR INCREASED TRANSLATION IN PLANT PLASTIDS

TECHNICAL FIELD

This invention relates to the application of genetic engineering techniques to plants. Specifically, the invention relates to compositions and methods for enhancing expression of proteins in plant plastids.

BACKGROUND

The plastids of higher plants are an attractive target for genetic engineering. Plant plastids (chloroplasts, amyloplasts, elaioplasts, etioplasts, chromoplasts, etc.) are the major biosynthetic centers that, in addition to photosynthesis, are responsible for production of industrially important compounds such as amino acids, complex carbohydrates, fatty acids, and pigments. Plastids are derived from a common precursor known as a proplastid and thus the plastids present in a given plant species all have the same genetic content. Plant cells contain 500–10,000 copies of a small 120–160 kilobase circular genome, each molecule of which has a large (approximately 25 kb) inverted repeat. Thus, it is possible to engineer plant cells to contain up to 20,000 copies of a particular gene of interest which potentially can result in very high levels of foreign gene expression. In addition, plastids of most plants are maternally inherited. Consequently, unlike heterologous genes expressed in the nucleus, heterologous genes expressed in plastids are not pollen disseminated, therefore, a trait introduced into a plant plastid will not be transmitted to wild-type relatives.

There remains a need for improved regulatory elements for expression of genes in a plant plastid. To date, the expression signals used routinely for plastid transgene expression derive from endogenous plastid genes. The plastid expression signals are typically derived from promoter regions of highly expressed plastid genes such as the promoter regions from the 16S ribosomal RNA operon (Prrn), psbA gene (PpsbA) or the rbcL gene (PrbcL). The psbA and rbcL genes are highly transcribed, but their translation is controlled by tissue-specific and light-regulated factors which limits their usefulness. In the case of Prrn, a synthetic ribosome binding site (RBS) patterned after the plastid rbcL gene leader has been typically used to direct translation. However, this Prrn/RBS is translated inefficiently due to poor ribosome binding.

A totally heterologous expression system has been used to express plastid genes (U.S. Pat. No. 5,576,198, the entirety of which is incorporated herein by reference). This system is a two component system. The first component is a plastid transgene driven by a T7 bacteriophage gene 10 promoter/leader sequence. The second component is a nuclear gene encoding the T7 Polymerase that is targeted to the plastid compartment. The limitation of this system is the need to create nuclear transformed lines that express the T7 Polymerase in preferred ways.

Plastids of higher plants present an attractive target for genetic engineering. As mentioned above, plastids of higher plants are maternally inherited. This offers an advantage for genetic engineering of plants for tolerance or resistance to natural or chemical conditions, such as herbicide tolerance, as these traits will not be transmitted to wild-type relatives. In addition, the high level of foreign gene expression is attractive for engineered traits such as the production of pharmaceutically important proteins.

Expression of nucleic acid sequences encoding for enzymes providing for herbicide tolerance as well as pharmaceutical proteins from plant plastid genome offers an attractive alternative to expression from the plant nuclear genome.

RELEVANT LITERATURE

McBride et al. U.S. Pat. No. 5,576,198 and McBride et al. (1994) *Proc Natl Acad Sci* 91:7301–7305 reports the plastid expression system based on a two component system utilizing a nuclearly encoded T7 polymerase targeted to the plastid which activates a transgene controlled by the T7 bacteriophage gene 10 promoter. Svab et al. (1990) *Proc Natl Acad Sci* 87:8526–8530 reports the standard chloroplast transforamtion methods. Svab, et al. (1993) *Proc Natl Acad Sci* 90:913–917 reports the use of the aadA gene for use in selection of transplastomic plants on spectinomycin and streptomycin, as well as integration sequences. Zoubenko et al. (1994) *Nuc Acid Res* 22:3819–3824 reports the construct of vectors for use in plastid transformation.

Barry, et al., U.S. Pat. No. 5,627,061 describes the cloning of EPSPS nucleotide sequences from several sources including *Agrobacterium strain* CP4 and methods for producing glyphosate tolerant plants. Kishore and Shah, *Ann. Rev. Biochem.* (1988) 57:627–663 reports the modification of DNA sequences for EPSPS for the enhancement of glyphosate tolerance. Stalker et al., U.S. Pat. No. 4,810,648 describes the cloning and use of a nucleic acid sequence encoding for the bromoxynil degrading gene, nitrilase.

SUMMARY OF THE INVENTION

The present invention provides nucleic acid sequences useful in enhancing expression of a wide variety of genes, both eukaryotic and prokaryotic, in plant plastids. Furthermore, plastid expression constructs are provided which are useful for genetic engineering of plant cells and which provide for enhanced expression of the EPSP synthase proteins or the hGH protein in plant cell plastids. The transformed plastids should be metabolically active plastids, and are preferably maintained at a high copy number in the plant tissue of interest, most preferably the chloroplasts found in green plant tissues, such as leaves or cotyledons.

The plastid expression constructs for use in this invention generally include a plastid promoter region capable of providing for enhanced expression of a DNA sequence, a DNA sequence encoding an EPSPS protein or hGH, and a transcription termination region capable of terminating transcription in a plant plastid.

The plastid promoter region of the present invention is preferably linked to a ribosome binding site which provides for enhanced translation of mRNA transcripts in a plant plastid.

The plastid expression construct of this invention is preferably linked to a construct having a DNA sequence encoding a selectable marker which can be expressed in a plant plastid. Expression of the selectable marker allows the identification of plant cells comprising a plastid expressing the marker.

In a preferred embodiment, vectors for transfer of the construct into a plant cell include means for inserting the expression and selection constructs into the plastid genome. This preferably comprises regions of homology to the target plastid genome which flank the constructs.

The constructs of the present invention preferably comprises a promoter sequence linked to a ribosome binding site capable of enhancing the translation of mRNA transcripts in the plant plastid. The ribosome binding site is preferrably derived from the T7 bacteriophage gene 10 leader sequence.

Of particular interest in the present invention is the high level of expression of nucleic acid sequences in plant pastids. Of particular interest is the high level expression of nucleic acid sequences encoding for enzymes involved in herbicide tolerance and encoding for pharmaceutical proteins.

The constructs of the present invention preferably comprises a DNA sequence encoding for a 5-Enolpyruvylshikimate-3-phosphate synthase (U.S. Pat. No. 5,633,435, the entirety of which is incorporated herein by reference), nitrilase, phytoene desaturase, aprotinin or a DNA sequence encoding Human Growth Hormone (U.S. Pat. No. 5,424,199, the entirety of which is incorporated herein by reference).

Plant cell plastids containing the constructs are also contemplated in the invention, as are plants, plant seeds, plant cells or progeny thereof containing plastids comprising the construct.

The present invention also includes methods for enhanced expression of DNA sequences in plant plastids.

The invention also includes a method for the enhanced expression of an enzyme conferring herbicide tolerance in a plant cell, by expressing the *Agrobacterium tumefaciens* sp strain CP4 EPSPS in plastids of the plant cell.

In addition, the invention also includes a method for the enhanced expression of an enzyme encoding hGH in plastids of the plant cell.

Thus, the present invention relates to a chimeric gene containing a herbicide tolerance coding sequence or the coding sequence of a pharmaceutical protein, a plant plastid expression vector containing a promoter operably linked to a T7 Bacteriophage Polymerase gene 10 ribosome binding site capable of enhanced expression in a plant plastid operably linked to a herbicide tolerance or pharmaceutical coding gene, a plant transformation vector having inserted therein a herbicide tolerance or pharmaceutical coding gene expressed from a plastid promoter linked to a T7 Bacteriophage Polymerase gene 10 ribosome binding site, plant cells transformed using such vectors and plants regenerated therefrom which exhibit a substantial degree of expression of nucleic acid sequences and proteins and methods for producing such plants and such plants.

BRIEF DESCRIPTION OF THE DRAWINGS

FIG. 1 shows the nucleotide sequence (SEQ ID NO:1) of the G10L ribosome binding site.

FIGS. 6A and 6B show a schematic of the expression construct pWRG4747.

FIG. 12 shows the mass spectrometry analysis for the RP-HPLC in FIG. 11.

DETAILED DESCRIPTION OF THE INVENTION

Figure 2:
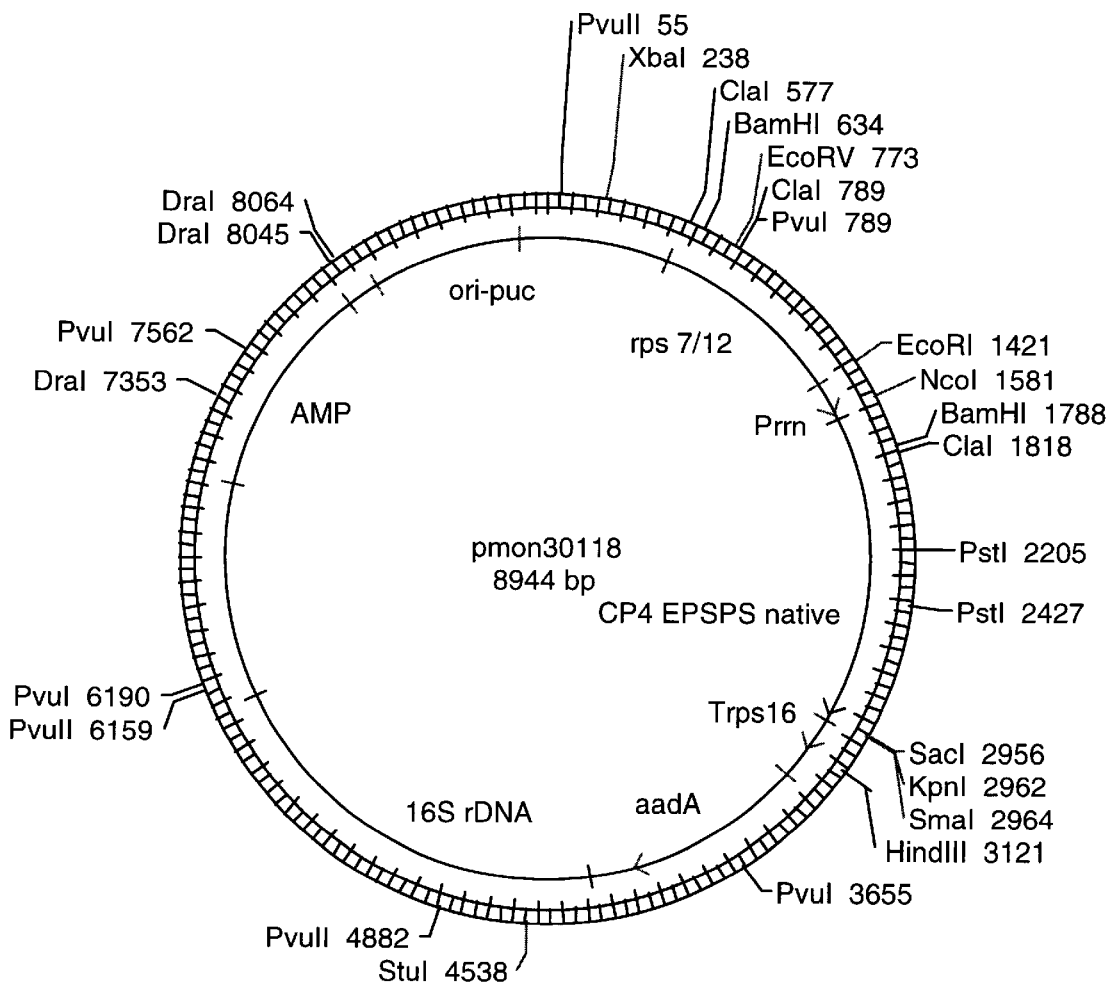
FIG. 2 shows a schematic of the plastid expression construct pMON30118.

In accordance with the subject invention, plastid expression constructs are provided which generally comprise a promoter functional in a plant plastid, a ribosome binding site derived from the T7 Bacteriophage Polymerase gene 10 leader, a DNA sequence encoding for a gene of interest, and a transcription termination region capable of terminating transcription in a plant plastid. These elements are provided as operably joined components in the 5' to 3' direction of transcription.

Furthermore, the constructs of the present invention may also include a nucleic acid sequence encoding a peptide capable of targeting said DNA sequence encoding a protein to the thylakoid lumen within the chloroplast.

Of particular interest in the present invention is the use of the plastid expression constructs to direct the high level transcription and translation (expression) of nucleic acid sequences. Such plastid expression constructs find use in directing the high level expression of DNA sequences encoding for enzymes involved in herbicide tolerance or encoding for the production of pharmaceutical proteins.

Of more particular interest in the present invention is the use of the plastid expression constructs to direct the high level translation of transcibed messenger RNA.

DNA sequence and biochemical data reveal a similarity of the plastid organelle's transcriptional and translational machineries and initiation signals to those found in prokaryotic systems. In fact, plastid derived promoter sequences have been reported to direct expression of reporter genes in prokaryotic cells. In addition, plastid genes are often organized into polycistronic operons as they are in prokaryotes.

Despite the apparent similarities between plastids and prokaryotes, there exist fundamental differences in the methods used to control gene expression in plastids and prokaryotes. As opposed to the transcriptional control mechanisms typically observed in prokaryotes, plant gene expression is controlled predominantly at the level of translation and mRNA stability by trans-acting nuclear encoded proteins.

Translation is a multi-stage process which first involves the binding of messenger RNA (mRNA) to ribosomes. Beginning at the translation start codon, the mRNA codons are read sequentially as the ribosomes move along the mRNA molecule. The specified amino acids are then sequentially added to the growing polypeptide chain to yield the protein or polypeptide encoded in the mRNA.

As mentioned, the first step in the translation process is the binding of the mRNA molecule to the ribosome. The nature of this interaction (i.e. binding) has been only partially elucidated. Analysis of RNase-resistant oligonucleotides isolated from bacterial translation initiation complexes indicate that a RNA fragment approximately 30 to 40 nucleotides in length comprises the initial ribosome binding site (RBS). Thus, a RBS is hereinafter understood to comprise a sequence of mRNA surrounding the translation start codon which is responsible for the binding of the ribosome and for initation of translation.

Recently, ribosome binding sites have been identified capable of directing translation in a prokaryotes. For example, a ribosome binding site derived from the T7 bacteriophage gene 10 leader, G10L (U.S. Pat. No. 5,232,840, the entirety of which is incorporated herein by reference) has been identified which enhances expression of nucleic acid sequences in prokaryotes.

Herbicides such as N-phosphonomethylglycine, halogenated hydroxybenzonitriles, and norflurazon have been the subject of a large amount of investigation.

N-phosphonomethylglycine, commonly referred to as glyphosate, inhibits the shikimic acid pathway which leads to the biosynthesis of aromatic compounds including amino acids, plant hormones and vitamins. Specifically, glyphosate curbs the conversion of phosphoenolpyruvic acid (PEP) and 3-phosphoshikimic acid to 5-enolpyruvyl-3-phosphoshikimic acid by inhibiting the enzyme 5-enolpyruvylshikimate-3-phosphate synthase (hereinafter referred to as EPSP synthase or EPSPS).

Glyphosate tolerant plants have been produced by transformation of various EPSP synthase genes into the nuclear genome of a plant. A gene for EPSP synthase has been cloned from *Agrobacterium tumefaciens* sp strain CP4 (U.S. Pat. No. 5,633,435) and confers a high level of glyphosate tolerance in plants Furthermore, high levels of glyphosate tolerance has been achieved in a number of crop plants by fusing EPSPS to a chloroplast transit peptide (CTP) for targeted expression in plastids. In addition, variants of the wild-type EPSPS enzyme have been isolated which are glyphosate tolerant as a result of alterations in the EPSPS amino acid coding sequence (Kishore and Shah, *Ann. Rev. Biochem.* (1988) 57:627–663; Shulze et al., *Arch. Microbiol.* (1984) 137:121–123; Kishore et al., *Fed. Proc.* (1986) 45:1506). These variants typically have a higher $K_i$ for glyphosate than the wild-type EPSPS enzyme which confers the glyphosate tolerant phenotype, but these variants are also characterized by a high $K_m$ for PEP which makes the enzyme kinetically less efficient (Kishore and Shah, *Ann. Rev. Biochem.* (1988) 57:627–663; Sost et al., *FEBS Lett.* (1984) 173: 238–241; Shulze et al., *Arch. Microbiol.* (1984) 137:121–123; Kishore et al., *Fed. Proc.* (1986) 45:1506; Sost and Amrhein, *Arch. Biochem. Biophys.* (1990) 282: 433–436).

In addition to engineering plants for glyphosate tolerance, plants have also been engineered to tolerate other classes of herbicides such as halogenated hydroxybenzonitriles, and norflurazon using nucleic acid sequences expressed in the nucleus.

Halogenated hydroxybenzonitriles, such as Bromoxynil, are suggested to act herbicidally by inhibiting the quinone-binding protein complex of photosystem II, inhibiting electron transfer (Van Rensen (1982) *Physiol. Plant* 54:515–520, and Sanders and Pallett (1986) *Pestic. Biochem. Physiol.* 26:116–122). Herbicides such as norflurazon inhibit the production of carotenoids.

Plants which are resistant to Bromoxynil have been produced by expressing DNA sequences encoding for enzymes capable of detoxifying Bromoxynil (nitrilases) in the plant cell nucleus. DNA sequences encoding for such nitrilases have been cloned from bacteria such as *Klebsiella pneumoniae* and used to construct vectors to direct the expression of the DNA sequence in plant cell nucleus (U.S. Pat. No. 4,810,648, the entirety of which is incorporated herein by reference).

Plants which are resistant to Norflurazon have been engineered by expressing nucleic acid sequences which encode for enzymes in the carotenoid biosynthetic pathway in plant cell nuclei. For example, by expressing a phytoene desaturase from *Erwinia uredovora* provides tolerance to norflurazon.

While plants transformed to express nucleic acid sequences encoding for such enzymes from the nuclear genome have found utility in engineering herbicide tolerant plants, it would be increasingly beneficial to obtain herbicide tolerant plants via plastidial expression.

In the examples provided herein, DNA sequences encoding for enzymes involved in herbicide tolerance are used in constructs to direct the expression of the sequences from the plant plastid. DNA sequences encoding for 5-enolpyruvylshikimate-3-phosphate synthase (EPSPS), bromoxynil nitrilase (Bxn), phytoene desaturase (crtI (Misawa et al, (1993) *Plant Journal* 4:833–840, and (1994) *Plant Jour* 6:481–489), and acetohydroxyacid synthase (AHAS (Sathasiivan et al. (1990) *Nucl. Acids Res.* 18:2188–2193)) are used in the expression constructs of the present invention to direct the expression of said herbicide tolerance nucleotide sequences from the plant plastid.

Transplastomic tobacco plants are identified which are homoplasmic for the DNA sequences of interest encoding said herbicide tolerance genes. Homoplasmic plants demonstrate a high level of protein expression from the plastid. Furthermore, homoplasmic plants demonstrate a high level of tolerance for the respective herbicide. For example, as described in more detail in the example below, plants transformed to express EPSPS from the plastid demonstrate a high level of tolerance for the herbicide glyphosate. In addition, homoplasmic tobacco lines expressing nitrilase or phytoene desaturase demonstrate high levels of tolerance for the herbicides bromoxynil and norflurazon, respectively.

An artisan skilled in the art to which the present invention pertains will recognize that additional sequences may be employed to in the plastid expression constructs of the instant invention to produce herbicide tolerant plants. Other nucleic acid sequence which may find use in the plastid expression constructs herbicide tolerant plants include the bar gene for tolerance to glufosinate (DeBlock, et al. (1987) *EMBO J.* 6:2513–2519).

Furthermore, additional glyphosate tolerance genes may be employed in the constructs of the present invention. Additional glyphosate tolerant EPSPS genes are described in U.S. Pat. No. 5,627,061, Padgette et al. (1996) Herbicide Resistant Crops, Lewis Publishers, 53–85, and in Penaloza-Vazquez, et al. (1995) *Plant Cell Reports* 14:482–487, the entireties of which are incorporated herein by reference.

It should be noted that the herbicide tolerance constructs of the present invention may also include sequences encoding genes involved in other stress tolerance genes, for example insect or disease resistance/tolerance genes. As described in more detail in the examples that follow, plastid expression constructs are used to regenerate plants which are resistant to the herbicide Buctril, which also expresses the *Bacillus thuringensis* cry1Ac protein.

In addition, the plastid expression constructs also find use in directing the production of human biological proteins (pharmaceutical proteins) from the plant plastid. Nucleic acid sequences encoding for the Human Growth Hormone (hGH) are employed in the plastid expression constructs of the present invention Furthermore, transplastomic tobacco plants containing such constructs demonstrate a high level of expression of hGH. In addition, the hGH protein expressed from the plant plastid exhibits characteristics of proper processing as well as proper protein folding.

Traditional methods of pharmaceutical protein production generally employ prokaryotic or single cell eukaryotic organisms for expression and large scale production systems. For example, production of the human biologic, Human Growth Hormone (U.S. Pat. No. 5,424,199), has been achieved in Bacillus and E. coli cells.

Another example is the production of aprotinin. Traditional methods for the production of aprotinin have employeed the expression of aprotinin in bacteria, or more usually, the extraction of the protein from bovine organs or tissues. Thus, there is a need in the art for an alternative approach for the large scale production of such human biologics.

Human Growth Hormone (hGH) participates in much of the regulation of normal human growth and development. This 22,000 dalton pituitary hormone exhibits a multitude of biological effects including linear growth (somatogenesis), lactation, activation of macrophages, insulin-like and diabetogenic effects among others (Chawla, Ann. Rev. Med. (1983) 34:519; Edwards, et al., Science (1988) 239:769; Thorner et al., J. Clin. Invest. (1988) 81:745). Growth deficiency in children leads to dwarfism, which has been successfully treated for more than a decade by exogenous administration of hGH. hGH is a member of a family of homologous hormones that include placental lactogens, prolactins, and other genetic and species variants or growth hormone (Nicoll, et al., Endocrine Reviews (1986) 7:169). hGH is unusual among these in that it exhibits broad species specificity and binds to either the cloned somatogenic (Leung, et al., Nature (1987) 33:537) or prolactin receptor (Boutin, et al., Cell (1988) 53:69).

Aprotinin (also known as bovine pancreatic trypsin inhibitor, BPTI) is a basic protein present in several bovine organs and tissues, sauch as the lymph nodes, pancreas, lungs, parotid gland, spleen and liver.

Aprotinin is known to inhibit variuos serine proteases, including trypsin, chymotrypsin, plasmin and kallikrein, and is used therapeutically in the treatment of acute pancreatitis, various stages of shock syndrome, hyperfibrinolytic hemorrhage and myocardial infarction. In addition, administration of aprotinin in high doses significantly reduces blood loss in connection with cardiac surgery, including cardiopulmonary bypass (Bidstrup, et al. (1989) Cardiovasc Surg. 44:640–645)

As demonstrated in more detail in the examples that follow, plastid expression constructs are employed to direct the expression of aprotinin and a human growth hormone from the plant plastid.

Other sequences which may find use in the production of human biologics include sequences encoding for insulin or insulin precursors may find use in the expression constructs of the present invention. The skilled artisan will recognize that many nucleotide sequences encoding for human biologics may be employed in the constructs of the present invention to direct their expression from a plant plastid such as thos described in Goodman and Gelman (1990) Pharmacological Basis of Therapeutics, Pergaman Press, $8^{th}$ Edition, Sections 14 and 15.

In developing the constructs the various fragments comprising the regulatory regions and open reading frame may be subjected to different processing conditions, such as ligation, restriction enzyme digestion, PCR, in vitro mutagenesis, linkers and adapters addition, and the like. Thus, nucleotide transitions, transversions, insertions, deletions, or the like, may be performed on the DNA which is employed in the regulatory regions or the DNA sequences of interest for expression in the plastids. Methods for restriction digests, Klenow blunt end treatments, ligations, and the like are well known to those in the art and are described, for example, by Maniatis et al. (in Molecular cloning: a laboratory manual (1989) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA or manipulation of the DNA by joining or removing sequences, linkers, or the like. Preferably, the vectors will be capable of replication to at least a relatively high copy number in E. coli. A number of vectors are readily available for cloning, including such vectors as pBR322, vectors of the pUC series, the M13 series vectors, and pBluescript vectors (Stratagene; La Jolla, Calif.).

In order to provide a means of selecting the desired plant cells, vectors for plastid transformation typically contain a construct which provides for expression of a selectable marker gene. Marker genes are plant-expressible DNA sequences which express a polypeptide which resists a natural inhibition by, attenuates, or inactivates a selective substance, i.e., antibiotic, herbicide etc.

Alternatively, a marker gene may provide some other visibly reactive response, i.e., may cause a distinctive appearance or growth pattern relative to plants or plant cells not expressing the selectable marker gene in the presence of some substance, either as applied directly to the plant or plant cells or as present in the plant or plant cell growth media.

In either case, the plants or plant cells containing such selectable marker genes will have a distinctive phenotype for purposes of identification, i.e., they will be distinguishable from non-transformed cells. The characteristic phenotype allows the identification of cells, cell groups, tissues, organs, plant parts or whole plants containing the construct.

Detection of the marker phenotype makes possible the selection of cells having a second gene to which the marker gene has been linked. This second gene typically comprises a desirable phenotype which is not readily identifiable in transformed cells, but which is present when the plant cell or derivative thereof is grown to maturity, even under conditions wherein the selectable marker phenotype itself is not apparent.

The use of such a marker for identification of plant cells containing a plastid construct has been described by Svab et al. (1993, supra). In the examples provided below, a bacterial aadA gene is expressed as the marker under the regulatory control of chloroplast 5' promoter and 3' transcription termination regions, specifically the regulatory regions of the psbA gene (described in Staub et al., EMBO J. (1993) 12(2):601–606). Numerous additional promoter regions may also be used to drive expression of the selectable marker gene, including various plastid promoters and bacterial promoters which have been shown to function in plant plastids.

Expression of the aadA gene confers resistance to spectinomycin and streptomycin, and thus allows for the identification of plant cells expressing this marker. The aadA gene product allows for continued growth and greening of cells whose chloroplasts comprise the selectable marker gene product. Cells which do not contain the selectable marker gene product are bleached. Selection for the aadA gene marker is thus based on identification of plant cells which are not bleached by the presence of streptomycin, or more preferably spectinomycin, in the plant growth medium.

A number of markers have been developed for use with plant cells, such as resistance to chloramphenicol, the aminoglycoside G418, hygromycin, or the like. Other genes which encode a product involved in chloroplast metabolism may also be used as selectable markers. For example, genes which provide resistance to plant herbicides such as glyphosate, bromoxynil or imidazolinone may find particular use. Such genes have been reported (Stalker et al., *J. Biol. Chem.* (1985) 260:4724–4728 (glyphosate resistant EPSP); Stalker et al., *J. Biol. Chem.* (1985) 263:6310–6314 (bromoxynil resistant nitrilase gene); and Sathasivan et al., *Nucl. Acids Res.* (1990) 18:2188 (AHAS imidazolinone resistance gene)).

Stable transformation of tobacco plastid genomes by particle bombardment is reported (Svab et.al. (1990), supra) and Svab et al. (1993), supra). The methods described therein may be employed to obtain plants homoplasmic for plastid expression constructs.

Generally, bombarded tissue is cultured for approximately 2 days on a cell division-promoting media, after which the plant tissue is transferred to a selective media containing an inhibitory amount of the particular selective agent, as well as the particular hormones and other substances necessary to obtain regeneration for that particular plant species. Shoots are then subcultured on the same selective media to ensure production and selection of homoplasmic shoots.

Transplastomic tobacco plants are analyzed for a pure population of transformed plastid genomes (homoplasmic lines). Homoplasmy is verified using Southern analysis employing nucleic acid probes spanning a region of the transgene and chloroplast genome (i.e. the insertion region). Transplastoimc plants which are heteroplasmic (i.e. contain a mixture of plastid genomes containing and lacking the transgene) are characterized by a hybridization pattern of wild type and transgenic bands. Homoplasmic plants show a hybridizatioin pattern lacking the wild type band.

Alternatively, homoplasmy may be verified using the polymerase chain reaction (PCR). PCR primers are utilized which are targeted to amplify from sequences from the insertion region. For example, a pair of primers may be utilized in a PCR reaction. One primer amplifies from a region in the transgene, while the second primer amplifies from a region proximal to the insertion region towards the insertion region. A second PCR reaction is performed using primers designed to amplify the region of insertion Transplastomic lines identified as homoplasmic produce the expected size fragment in the first reaction, while they do not produce the predicted size fragment in the second reaction.

Where transformation and regeneration methods have been adapted for a given plant species, either by Agrobacterium-mediated transformation, bombardment or some other method, the established techniques may be modified for use in selection and regeneration methods to produce plastid-transformed plants. For example, the methods described herein for tobacco are readily adaptable to other solanaceous species, such as tomato, petunia and potato.

For transformation of soybean, particle bombardment as well as Agrobacterium-mediated nuclear transformation and regeneration protocols have been described (Hinchee et al. U.S. Pat. No. 5,416,011, and Christou et al. U.S. Pat. No. 5,015,580). The skilled artisan will recognize that protocols described for soybean transformation may be used.

In Brassica, Agrobacterium-mediated transformation and regeneration protocols generally involve the use of hypocotyl tissue, a non-green tissue which might contain a low plastid content. Thus, for Brassica, preferred target tissues would include microspore-derived hypocotyl or cotyledonary tissues (which are green and thus contain numerous plastids) or leaf tissue explants. While the regeneration rates from such tissues may be low, positional effects, such as seen with Agrobacterium-mediated transformation, are not expected, thus it would not be necessary to screen numerous successfully transformed plants in order to obtain a desired phenotype.

For cotton, transformation of *Gossypium hirsutum L.* cotyledons by co-cultivation with *Agrobacterium tumefaciens* has been described by Firoozabady et al., *Plant Mol. Bio.* (1987) 10:105–116 and Umbeck et al., *Bio/Technology* (1987) 5:263–266. Again, as for Brassica, this tissue may contain insufficient plastid content for chloroplast transformation. Thus, as for Brassica, an alternative method for transformation and regeneration of alternative target tissue containing chloroplasts may be desirable, for instance targeting green embryogenic tissue.

Other plant species may be similarly transformed using related techniques. Alternatively, microprojectile bombardment methods, such as described by Klein et al. (*Bio/Technology* 10:286–291) may also be used to obtain nuclear transformed plants comprising the viral single subunit RNA polymerase expression constructs described herein. Cotton transformation by particle bombardment is reported in WO 92/15675, published Sep. 17, 1992. Suitable plants for the practice of the present invention include, but are not limited to, soybean, cotton, alfalfa, oil seed rape, flax, tomato, sugar beet, sunflower, potato, tobacco, maize, wheat, rice and lettuce.

The vectors for use in plastid transformation preferably include means for providing a stable transfer of the plastid expression construct and selectable marker construct into the plastid genome. This is most conveniently provided by regions of homology to the target plastid genome. The regions of homology flank the construct to be transferred and provide for transfer to the plastid genome by homologous recombination, via a double crossover into the genome. The complete DNA sequence of the plastid genome of tobacco has been reported (Shinozaki et al., *EMBO J*. (1986) 5:2043–2049). Complete DNA sequences of the plastid genomes from liverwort (Ohyama et al., *Nature* (1986) 322:572–574) and rice (Hiratsuka et al., *Mol. Gen. Genet.* (1989) 217:185–194), have also been reported.

Where the regions of homology are present in the inverted repeat regions of the plastid genome (known as IRA and IRB), two copies of the transgene are expected per transformed plastid. Where the regions of homology are present outside the inverted repeat regions of the plastid genome, one copy of the transgene is expected per transformed plastid. The regions of homology within the plastid genome are approximately 1 kb in size. Smaller regions of homology may also be used, and as little as 100 bp can provide for homologous recombination into the plastid genome. However, the frequency of recombination and thus the frequency of obtaining plants having transformed plastids decreases with decreasing size of the homology regions.

Examples of constructs having regions of homology the plastid genome are described in Svab et.al. (1990 supra), Svab et al. (1993 supra) and Zoubenko et al. (*Nuc Acid Res* (1994) 22(19):3819–3824).

As described in more detail in the examples below, constructs are described which provide for enhanced expression of DNA sequences in plant plastids. Various promoter/ribosome binding site sequences are employed to direct expression in plant plastids. Promoter sequences of the 16S ribosomal RNA operon (Prrn) are linked to a ribosome binding site (RBS) derived from the T7 bacteriophage gene 10 leader sequence (G10L). DNA sequences expressed under the regulatory control of the Prrn/G10L sequence show a significantly higher level of protein expression than those levels obtained under the control of other promoter/RBS combinations, while expression of mRNA may or may not be higher in these plants.

In the examples below, nucleic acid sequences encoding CP4 EPSP synthase (U.S. Pat. No. 5,633,435) are placed into expression constructs for expression of EPSP synthase enzyme from the plant plastid. Furthermore, a DNA sequence encoding for hGH (U.S. Pat. No. 5,424,199) is also placed into expression construct for the expression of human growth hormone from the plant plastid. The constructs prepared utilize a ribosome binding site designed after the T7 bacteriophage gene 10 leader (G10L) to increase the expression of the nucleic acid sequences in the plant plastid.

Plastid expression constructs encoding for the expression of EPSPS and hGH are introduced via a chloroplast transformation vector.

Tobacco lines containing the native encoding sequence to the EPSPS enzyme expressed in plastids under the control of the Prrn/G10L promoter/ribosome binding site sequence demonstrate a significantly higher level of protein expression than those levels obtained from EPSPS expressed under the control of the Prrn/rbcL RBS sequence. However, EPSPS mRNA is expressed at a higher level in plants expressing CP4 EPSPS from the plastid under the control of the Prrn/rbcL(RBS). These results indicate that translation from transcripts containing the T7 bacteriophage gene 10 ribosome binding site is more efficient. In addition, protein expression levels of EPSPS obtained from transplastomic tobacco lines expressing EPSPS under the control of the Prrn/G10L RBS provide for a high level of glyphosate tolerance.

Furthermore, transplastomic tobacco lines transformed to express hGH under the control of the Prrn/G10L promoter/ribosome binding site sequence demonstrate a significantly higher level of protein expression than those levels obtained from hGH expressed under the control of the PpsbA promoter/RBS sequence.

Increases in protein expression levels of at least approximately 200 fold may be obtained from constructs utilizing Prrn/G10L ribosome binding site for expression of EPSPS and hGH over the expression levels obtained from other promoter/RBS combinations for plastid expression. In addition, protein levels obtained from plastid expression constructs utilizing the Prrn/G10L promoter/RBS sequence may accumulate 50 to 3500 fold higher levels than from nuclear expression constructs. Thus, inclusion of the G10L ribosome binding site in plastid expression constructs may find use for increasing the levels of protein expression from plant plastids.

Furthermore, the constructs of the present invention may also include sequences to target the expressed protein to a particular suborganellar region, for example, the thylakoid lumen of the chloroplast. For example, as described in the examples below, a nucleotide sequence encoding a peptide from the plastid genome cytochrome ƒ targets the expressed aprotinin protein to the thylakoid membrane. Such targeting of expressed proteins may provide for a compartmentalization of the protein allowing for increased oxidative stability and proper protein folding.

The invention now being generally described, it will be more readily understood by reference to the following examples which are included for purposes of illustration only and are not intended to limit the present invention.

EXAMPLES

Example 1 Expression Constructs

Constructs and methods for use in transforming the plastids of higher plants are described in Zoubenko et al. (*Nuc Acid Res* (1994) 22(19):3819–3824), Svab et al. (*Proc. Natl. Acad. Sci.* (1990) 87:8526–8530 and *Proc. Natl. Acad. Sci.* (1993) 90:913–917) and Staub et al. (*EMBO J.* (1993) 12:601–606). Constructs and methods for use in transforming plastids of higher plants to express DNA sequences under the control of a nuclearly encoded, plastid targeted T7 polymerase are described in U.S. Pat. No. 5,576,198. The complete DNA sequences of the plastid genome of tobacco are reported by Shinozaki et al. (*EMBO J.* (1986) 5:2043–2049). All plastid DNA references in the following description are to the nucleotide number from tobacco.

The complete nucleotide sequence encoding the tobacco cytochrome ƒ (ɛtA) is described in Bassham et al, (1991) *J Biol Chem* 266:23606–23610 and Konishi et al. (1993) *Plant Cell Physiol* 34:1081–1087.

1A. Promoter/Ribosome Binding Site Sequences

The promoter region of the plastid 16S ribosomal RNA operon (Prrn) is linked to a synthetic ribosome binding site (RBS) patterned on the plastid rbcL gene leader to create the Prrn/rbcLRBS fragment. The Prrn/rbcLRBS sequence is as described in Svab et al. (1993, supra) for the Prrn/rbcL(S) fragment.

The promoter region of the plastid psbA promoter (PpsbA) and terminator sequences (TpsbA) are described in Staub et al. (1993, *EMBO J.*, 12, 601–606).

The Prrn/G10L sequence was constructed by annealing two oligonucleotide sequences, T7lead1 and T7lead2 (Table 1), to create the G10L plastid ribosome binding site (FIG. 1). The G10L sequence was ligated to the 3' terminus of the Prrn promoter sequence as an EcoRI/NcoI fragment to create the Prrn/G10L sequence.

TABLE 1

T7lead1
5'-AAT TGT AGA AAT AAT TTT GTT TAA CTT TAA
GAA GGA GAT ATA CC-3' (SEQ ID NO:4)

T7lead2
5'-CAT GGG TAT ATC TCC TTC TTA AAG TTA AAC
AAA ATT ATT TCT AC-3' (SEQ ID NO:3)

Chimeric genes are preferably inserted into the expression vector to direct their transcription from the Prrn promoter. Thus, in the plastid genome, chimeric genes are transcribed from the Prrn/RBS promoter, or the Prrn/G10L promoter in the plant plastid.

1B. CP4 EPSPS Plastid Expression Constructs

A plastid expression vector pMON30117 is constructed from a precursor vector pPRV111B (Zoubenko, et al. 1994, supra, GenBank accession U12813). The vector pMON30117 carries a multiple cloning site for insertion of a passenger gene in a Prrn/rbcLRBS/Trps16 expression cassette. The Prrn/rbcLRBS sequence is cloned into pPRV111B vector as an EcoRI/NcoI fragment, and the terminator region from the plastid rps16 gene (Trps16) is cloned 3' of the Prrn promoter as a HindIII/NcoI fragment. The Trps16 fragment comprises the rps16 gene 3'-regulatory region from nucleotides 5,087 to 4,939 in the tobacco plasmid DNA.

The pPRV111B backbone of the vector pMON30117 contains a marker gene, aadA, for selection on spectinomycin and streptomycin, and rps 7/12 for the integration, by homologous recombination, of the passenger DNA into trnV-rps7/12 intergenic region.

The plastid expression construct pMON30118 (FIG. 2) was prepared by cloning the native CP4 EPSPS gene fused with the N-terminal five (5) amino acids from the plastid rbcL (described in Svab et al., 1993 supra) gene as an NcoI/SmaI fragment into the multiple cloning site of the vector pMON30117.

Figure 3:
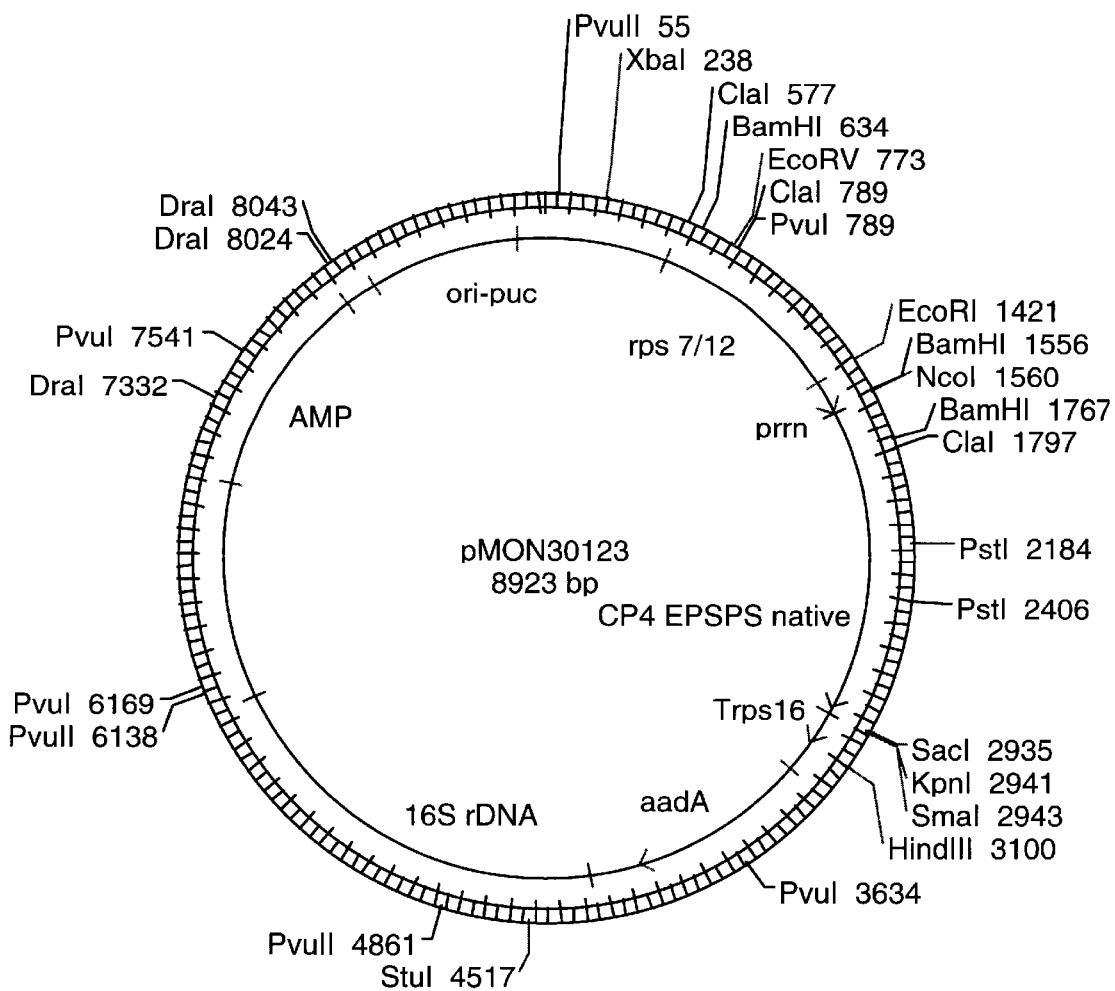
FIG. 3 shows a schematic of the plastid expression construct pMON30123.

The plastid expression construct pMON30123 (FIG. 3) is essentially the same as pMON30118 with the exception of the deletion of the N-terminal five (5) amino acids from the plastid rbcL.

Figure 4:
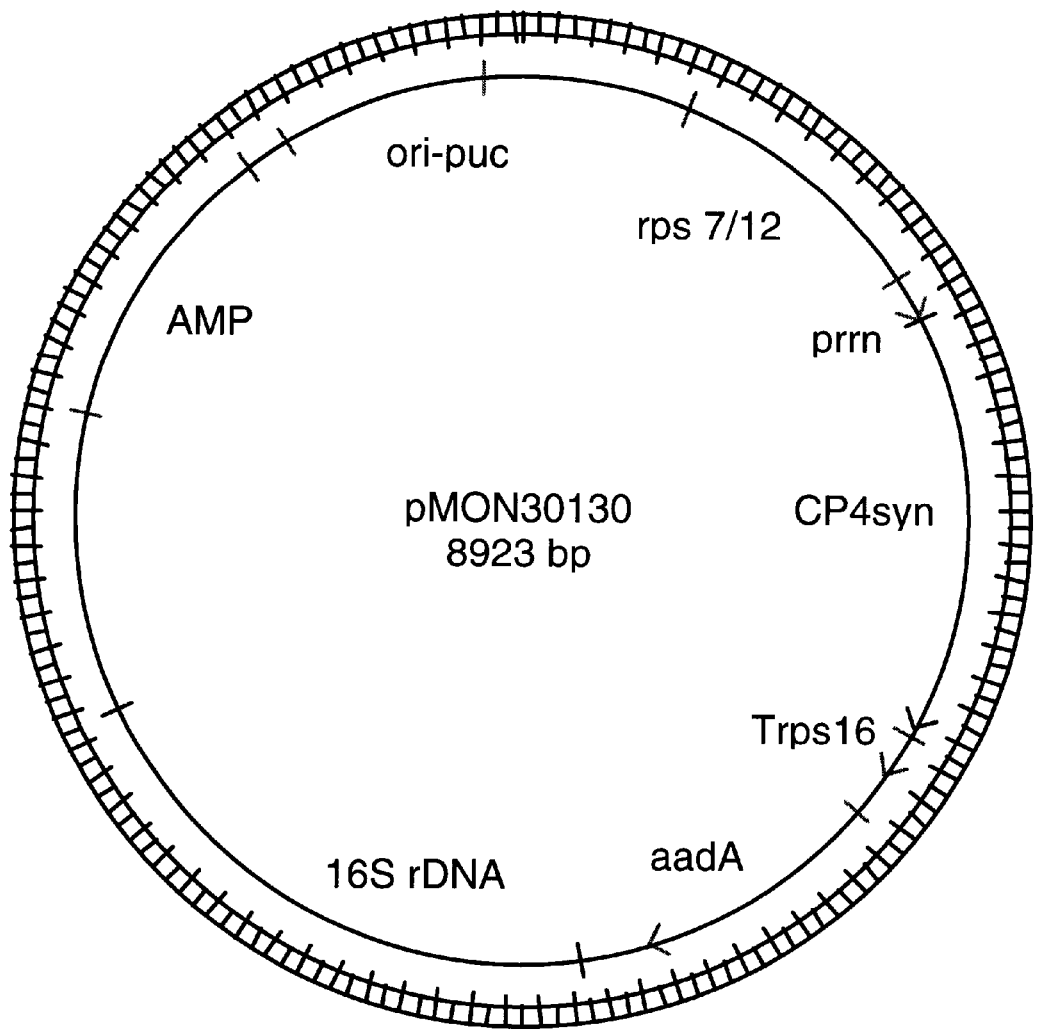
FIG. 4 shows a schematic of the plastid expression construct pMON30130.

The plastid expression construct pMON30130 (FIG. 4) was created by replacing the native CP4 EPSPS of pMON30123, with a synthetic CP4 gene. This construct also lacks the N-terminal 5 amino acid fusion from the plastid rbcL gene.

Figure 5:
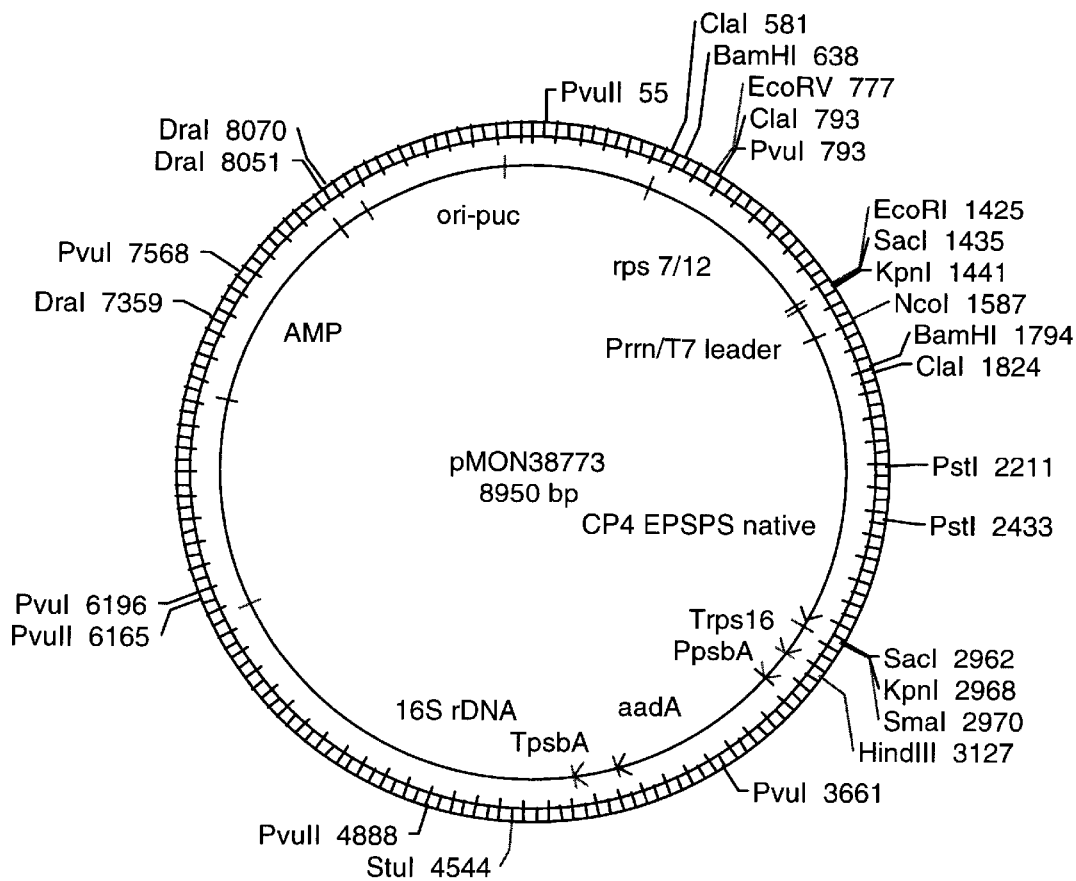
FIG. 5 shows a schematic of the plastid expression construct pMON38773.

The plastid expression construct pMON38773 (FIG. 5) was constructed by replacing the Prrn/RBS sequence of pMON30123 with the Prrn/G10L promoter sequence described above. The EPSPS DNA sequence of pMON38773 also lacks the N-terminal 5 amino acid fusion from the plastid rbcL gene.

A plastid expression construct, pMON38766 was constructed using the promoter from T7 phage gene 10 (P-T7), including G10L, CP4 (native) gene coding region, and the terminator sequence from plastid rps16 gene (Trps16).

A plastid expression construct, pMON38797 was constructed using the promoter from T7 phage gene 10 (P-T7), including G10L, CP4 (synthetic) gene coding region, terminator from plastid rps16 gene (Trps16).

A plastid expression construct, pMON38798 was constructed using the promoter of the 16SrDNA operon (Prrn), G10L, CP4 (synthetic) gene coding region, terminator from plastid rps16 gene (Trps16).

A plastid expression construct, pMON38793 was constructed using the promoter of the 16SrDNA operon (Prrn), a synthetic ribosome binding site (RBS) patterned from the plastid rbcL gene, the glyphosate tolerant Petunia EPSP synthase gene (P-EPSPS, Padgette, et al. (1987) Arch. Biochem. Biophys. 258:564–573) carrying the mutation Glycine to Alanine at amino acid position 101, terminator from plastid rps16 gene (Trps16).

A plastid expression construct, pMON38796 was constructed using the promoter of the 16SrDNA operon (Prrn), synthetic ribosome binding site (RBS) patterned from the plastid rbcL gene, the glyphosate tolerant Achromobacter (strain LBAA) EPSP synthase gene (U.S. Pat. No. 5,627,061, the entirety of which is incorporated herein by reference)carrying the mutation Glycine to Alanine at amino acid position 100, terminator from plastid rps16 gene (Trps16).

A plastid expression construct, pMON45204, was constructed using the promoter of the 16SrDNA operon (Prrn) with the G10L, the glyphosate tolerant Pseudomonas (strain LBAA) EPSP synthase gene carrying the mutation Glycine to Alanine at amino acid position 100, terminator from plastid rps16 gene (Trps16).

A plastid expression construct, pMON45201, was constructed using the promoter of the 16SrDNA operon (Prrn), synthetic ribosome binding site (RBS) patterned from the plastid rbcL gene, wild-type glyphosate tolerant Bacillus subtilis aroE (EPSPS) (U.S. Pat. No. 5,627,061) gene, terminator from plastid rps16 gene (Trps16).

1C. Bucril (bxn) Plastid Expression Constructs

The bxn herbicide resistance gene (U.S. Pat. No. 4,810,648, the entirety of which is incorporated herein by reference) was removed from the plasmid pBrx47 as an Nco I to Asp718 restriction fragment and cloned into Nco/Asp718 cut pUC120 resulting in plasmid pBrx87. Plasmid pBrx87 was then digested with Nco/Xba and cloned into the Nco/Xba sites of the plasmid pLAA21 which contains the Prrn plastid promoter and the rpsL 3' region for plastid expression. The resulting plasmid was designated pBrx89. Plasmid pBrx89 was digested with Sac I and Hind III and the 1.5 kb chimeric bxn gene with plastid expression signals was inserted into the Sac/Hind III sites of the tobacco plastid homology vector pOVZ44B (Zoubenko et al, Nuc Acids Res 22: 3819–3824 (1994)) to create plasmid pCGN5175.

To construct plasmid pCGN6114, plasmid pBrx90 (a Bluescript plasmid containing the bxn gene encoding the bromoxynil specific nitrilase) was digested with Nco I/Asc I and the bxn structural gene was substituted for the GUS gene in the Nco/Asc digested plasmid pCGN5063 resulting in plasmid pCGN6107. This plasmid contains the the bxn gene under the control of the T7 promoter/gene 10 leader at the 5' end and the psbA/T7 hybrid transcriptional terminator at the 3' end of the chimeric gene. This T7 promoter/bxn chimeric gene was excised from pCGN6107 as a Hind III/Not I DNA segment and moved into the choromphenical plasmid BCSK+ (Stratagene) at the Hind III/Not sites to create plasmid pCGN6109. The chimeric gene was them moved as a Hind III/Not fragment from pCGN6109 into the chloroplast homology vector pOVZ44B described above to create plasmid pCGN6114. Tobacco plants transformed with pCGN6114 require the T7 RNA polymerase be provided in the plant plastid background to activate transcription of the chimeric bxn gene via the T7 promoter. This system has previously been detailed in McBride et al PNAS 91:7301–7305 (1994) and McBride et al U.S. Pat. No. 5,576,198.

1D. BXN/AHAS Plastid Expression Constructs

A plastid expression construct, pCGN5026, is prepared to direct the expression of BXN and AHAS from the plant plastid. The AHAS nucleotide sequence (described in EP Publication Number 0 525 384 A2, the entirety of which is incorporated herein by reference) is translationally linked to the BXN nucleotide sequence (U.S. Pat. No. 4,810,648, the entirety of which is incorporated herein by reference) The AHAS structural gene encoding acetohydroxyacid synthase was cloned from the plasmid pCGN4277 as an Nco I to Age DNA fragment into the Nco/Xma sites of plasmid pUC120 to create plasmid pCGN5022. This plasmid was then digested with the enzymes BamH I and Pst and a 1.3 kb Bam/Pst DNA segment containing the bxn gene encoding the bromoxynil-specific nitrilase was excised from the plasmid pBrx26 and cloned into the Bam/Pst sites of pCGN5022 to create plasmid pCGN5023. Plasmid pCGN5023 contained a 3.3 kb DNA segment containing the AHAS/bxn operon segment and this fragment. This plasmid was cut at the unique Pst site and this Pst site was removed and replaced with a synthetic linker containing a unique Xba I restriction site generating plasmid pCGN5024. Plasmid pCGN5024 was digested with Nco/Xba and the 3.3 kb Nco/Xba DNA fragment was cloned into the plastid promoter cassette vector pLAA21(Pst) that had been digested with Nco and Xba to remove the GUS gene. The plasmid resulting from this cloning was designated plasmid pCGN5025 and contained the herbicide operon under the control of the plastid promoter Prrn and the rpsL 3' DNA segment. The entire chimeric herbicide operon under the control of the plastid expression elements was excised from pCGN5025 as a Sac I/Pst DNA fragment and cloned into the Sac/Pst sites of the plastid homology cassette vector pOVZ44B (Zoubenko et al, *Nuc Acids Res* 22:3819–3824 (1994)) to facilitate transfer into the tobacco chloroplast genome.

1E. Bt cry1Ac and bxn Plastid Expression Construct

Plasmid pBrx9 (Stalker and McBride, (1987) *J Bacteriol* 169:955–960), an original clone from Klebsiella containing a bxn gene DNA segment, was used as a template to generate an ~450 bp BamH I/Cla I PCR DNA fragment that encompasses the N-terminal end of the bxn gene and includes 44 bp of the 5' untranslated portion of the native gene. This fragment was exchanged with the ~400 bp Bam/Cla fragment in the plasmid pBrx90 resulting in plasmid pBrx90.1. This plasmid contains the entire bxn gene and the 44 bp untranslated 5' DNA segment. The bxn gene was excised from plasmid pBrx90.1 as a Bam/Asc I DNA segment and inserted into plasmid pCGN5146 at the Bgl II/Asc I sites to generate plasmid pCGN5191. Plasmid pCGN5146 is a pKK233-2 (Pharmacia) derivative containing the full-length cryIAc gene encoding the HD-73 Bt protoxin. Plasmid pCGN5191 then contains the cryIAc and bxn genes in an operon configuration with the bxn gene being the distal gene in the operon. Both genes are under the control of the Ptac promoter for *E coli* expression in 5191. Plasmid pCGN5191 was digested with Nco/Asc and the Nco/Asc DNA fragment containing the Bt/bxn operon was cloned into the Nco/Asc sites of the chloroplast homology vector pCGN5155, a derivative of pOVZ44B. The resulting plasmid, pCGN5197 contains the Bt/bxn operon under the control of the Prrn plastid promoter and rpsL transcription terminator regions. This plasmid facilitated transfer of the Bt/bxn chimeric operon into the tobacco plastid genome.

1F. Phytoene Desaturase Plastid Expression Constructs

The crtI gene was obtained as a Hind III/Sal I PCR fragment from the original plasmid containing the Erwinia carotova crt operon (Misawa et al, (1994) *Plant Jour* 6:481–489)) and cloned as a Hind III/Sal DNA segment into BCSK+ (Stratagene) at the Hind III/Sal sites to generate plasmid pCGN5172. The crtI fragment was cloned from pCGN5172 as an Nco I/Sal I fragment into pCGN5038 (a derivative of pOVZ44B) to create the plastid expression construct pCGN5177. This construct directs the expression of the crtI sequence from the Prrn promoter and the rps16 terminator sequence. This plasmid facilitated the transfer of the chimeric crtI gene into the tobacco plastid genome.

1G. hGH Expression Constructs for Plant Transformation

Nuclear Expression Constructs

Figure 6A:
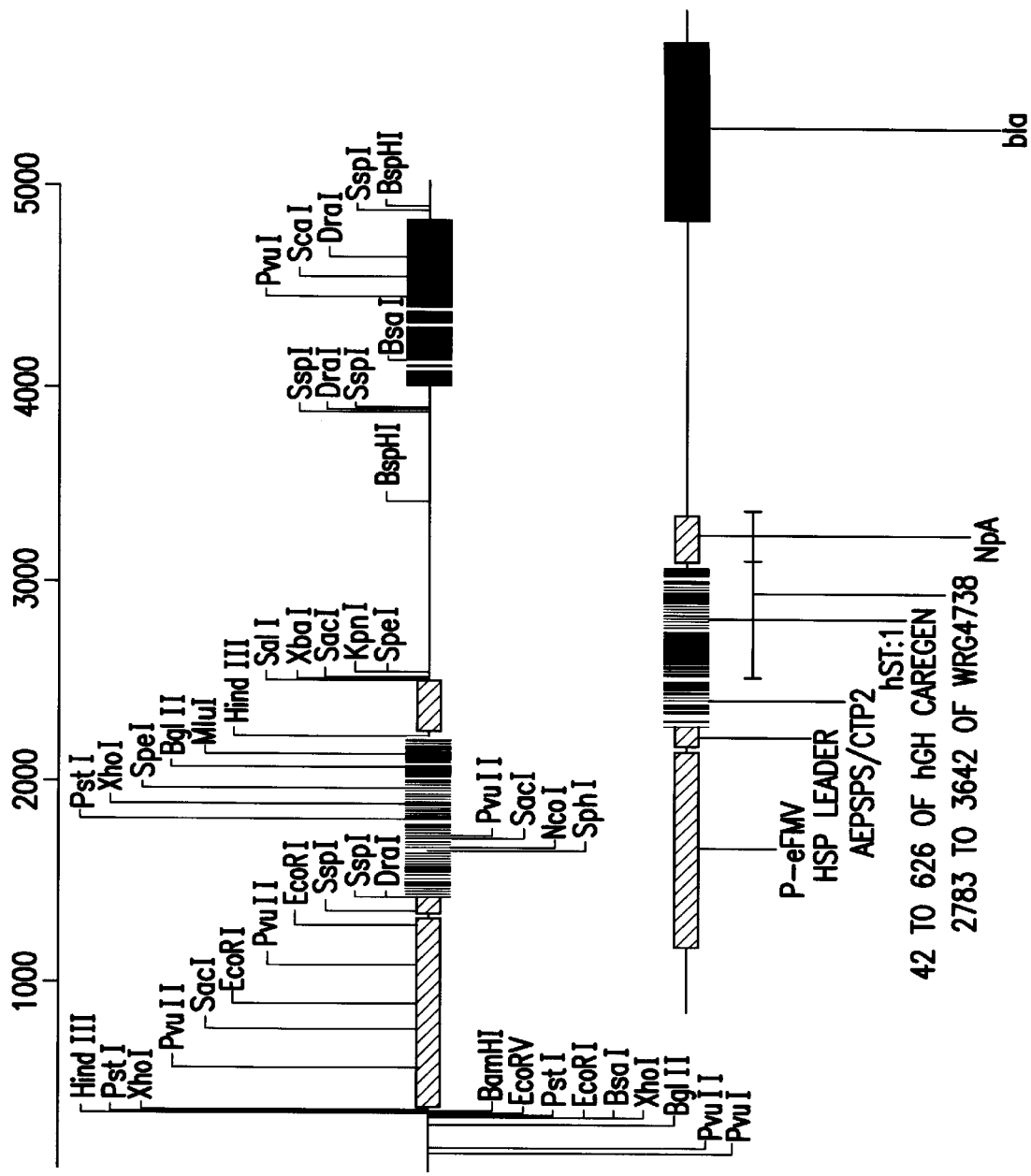

The construct pWRG4747 (FIG. 6) was constructed to direct the expression of hGH in the plant nuclear genome. This vector contains the hGH operably linked to the Figwort Mosaic Virus promoter (U.S. Pat. No. 5,378,619, the entirety is incorporated herein by reference) and the CTP2 leader for directing the hGH protein into the plastid. The FMV/CTP2L::hGH::NpA fragment is cloned along with the DNA sequence conferring resistance to Kanamycin between the right and left borders (RB and LB) of the transfer DNA (tDNA) of *Agrobacterium tumefaciens* to direct the integration into the nuclear genome.

The nuclear transformation vector pWRG4744 contains essentially the same elements as pWRG4747 except the construct lacks the CTP2 leader and the hGH protein is directed to the plant cell cytoplasm.

Plastid Expression Constructs

Figure 7A:
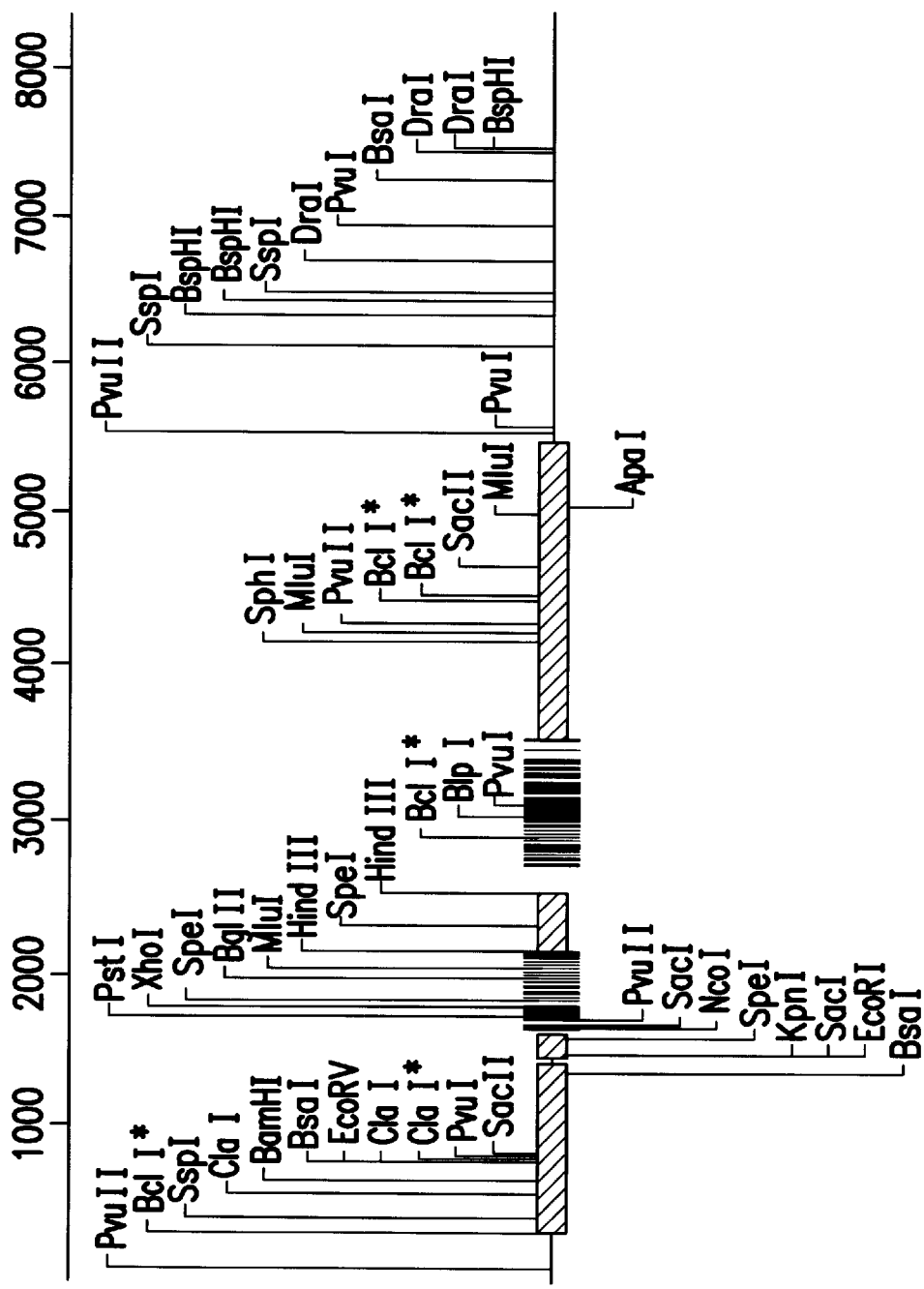
FIGS. 7A and 7B show a schematic of the plastid expression vector pWRG4838.
Figure 7B:
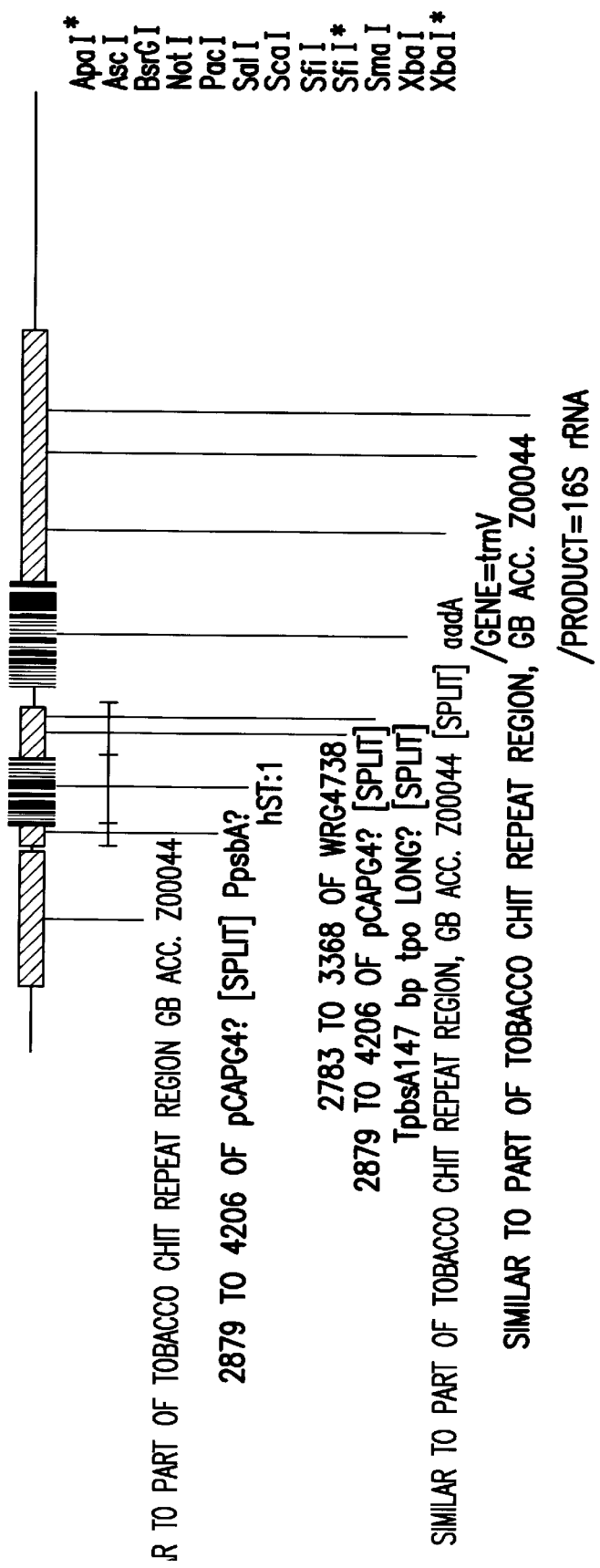

The plastid expression vector pWRG4838 (FIG. 7) was constructed using the full length hGH gene expressed from the promoter region from the psbA gene and the psbA gene terminator, PpsbA and TspbA respectively (described in Staub et al. (1993), supra). This chimeric promoter-gene-terminator fusion (PpsbA::hGH::TpsbA) is cloned adjacent to the selectable marker gene aadA also driven by the plastid expression elements of the psbA gene. The two chimeric gene sequences are cloned into a vector between two sequences which direct the integration of the chimeric gene sequences into the tobacco plastid genome upstream of the plastid 16SrDNA. This is joined to a 1 kb Ampicillin resistance gene which provides for selection of *E. coli* containing the construct and the pUC origin of replication for plasmid maintenance in *E. coli*.

Figure 8:
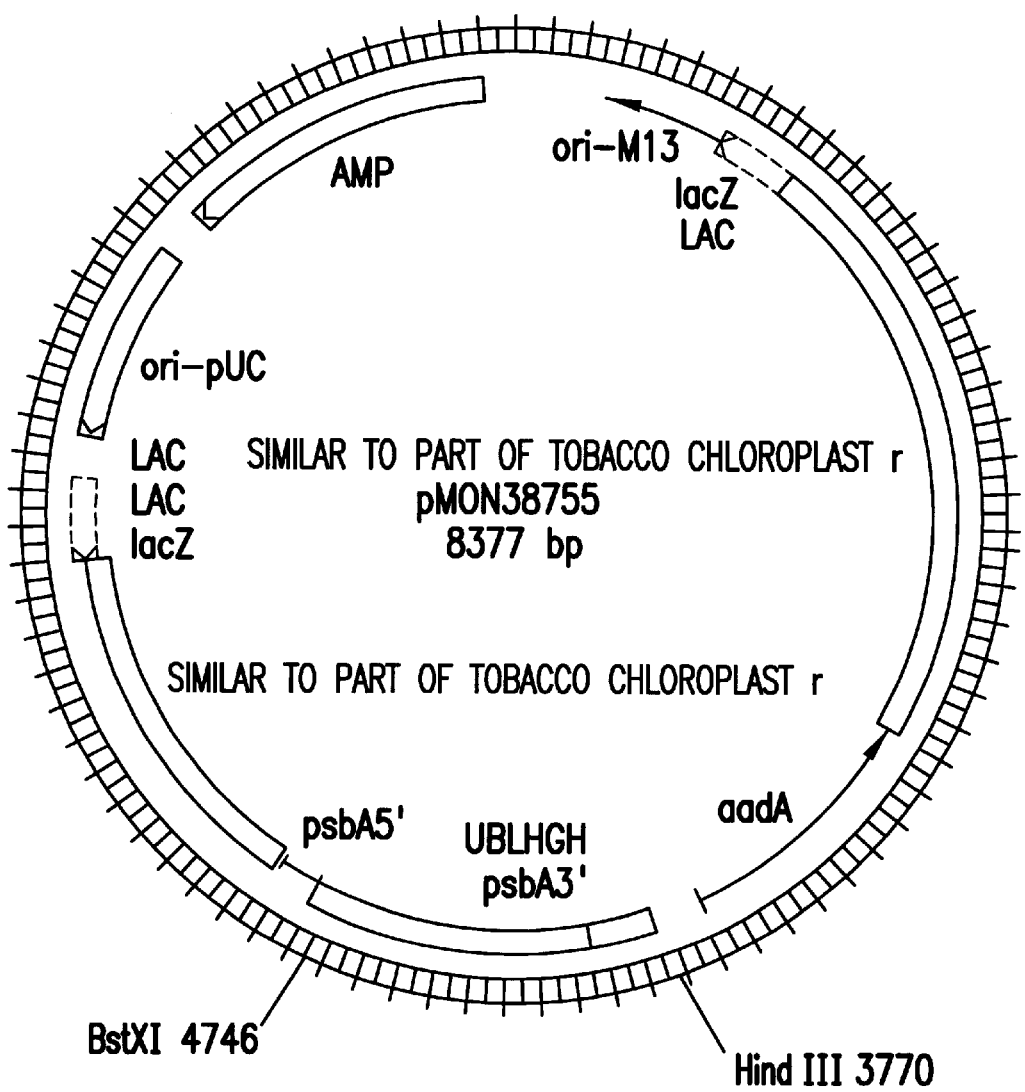
FIG. 8 shows a schematic of the plastid expression construct pMON38755.

The plastid expression construct pMON38755 (FIG. 8) was prepared using the hGH DNA sequence translationally fused at the N-terminus with the yeast ubiquitin gene, creating the Ubi-hGH fusion gene. The Ubi-hGH fusion gene is cloned next to the aadA gene for selection of transplastomic tobacco on media containing spectinomycin or streptomycin (from pPRV112B described in Zoubenko et al. (1994) supra). Sequences are included for the homologous recombination of sequences encoding for hGH and aadA expression. These sequences are obtained from the vector pPRV112B described in Zoubenko et al. (1994, supra). This is joined to a 1 kb Ampicillin resistance gene which provides for selection of *E. coli* containing the construct and the pUC origin of replication for plasmid maintenance in *E. coli*.

Figure 9:
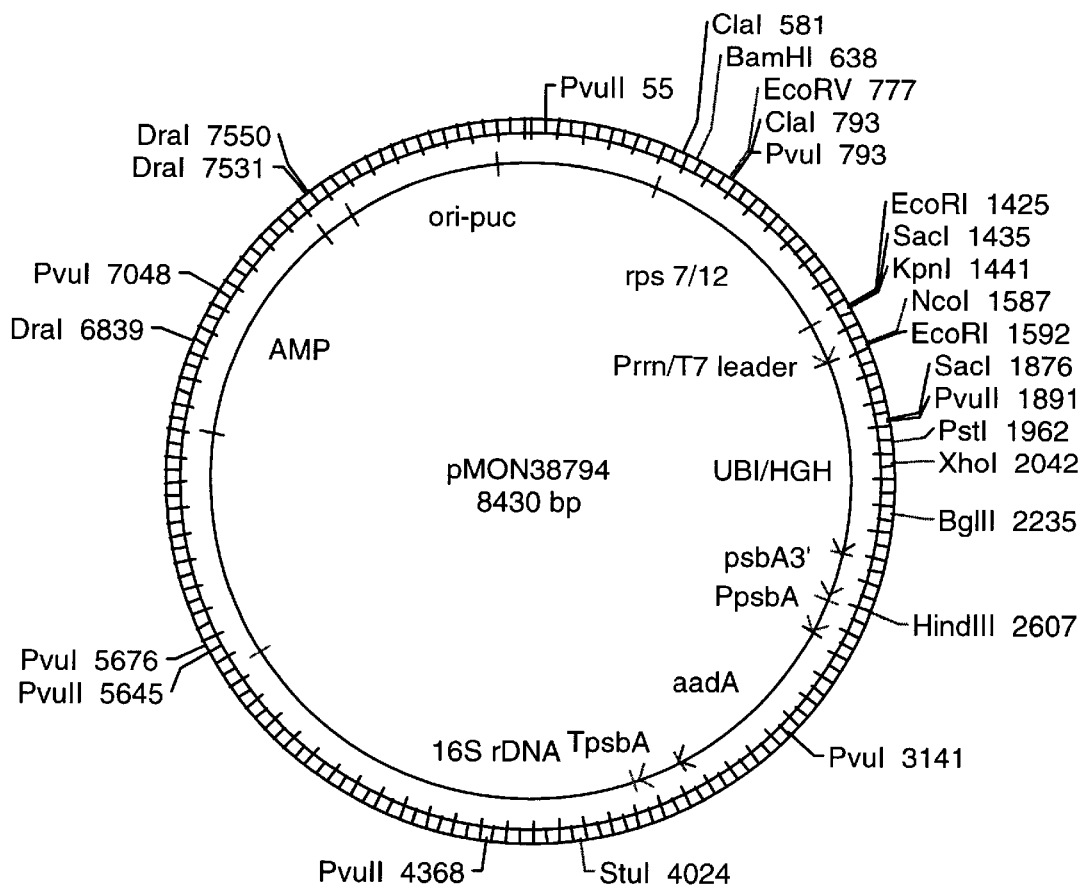
FIG. 9 shows a schematic of the plastid expression construct Pmon38794.

The plastid expression construct pMON38794 (FIG. 9) contains essentially the same elements as pMON38755, with the following exception. The 0.15 kb psbA promoter sequence is replaced with the Prrn/G10L promoter sequence described above.

1H. Constructs for the Expression of Aprotinin in Plastids.

Figure 10:
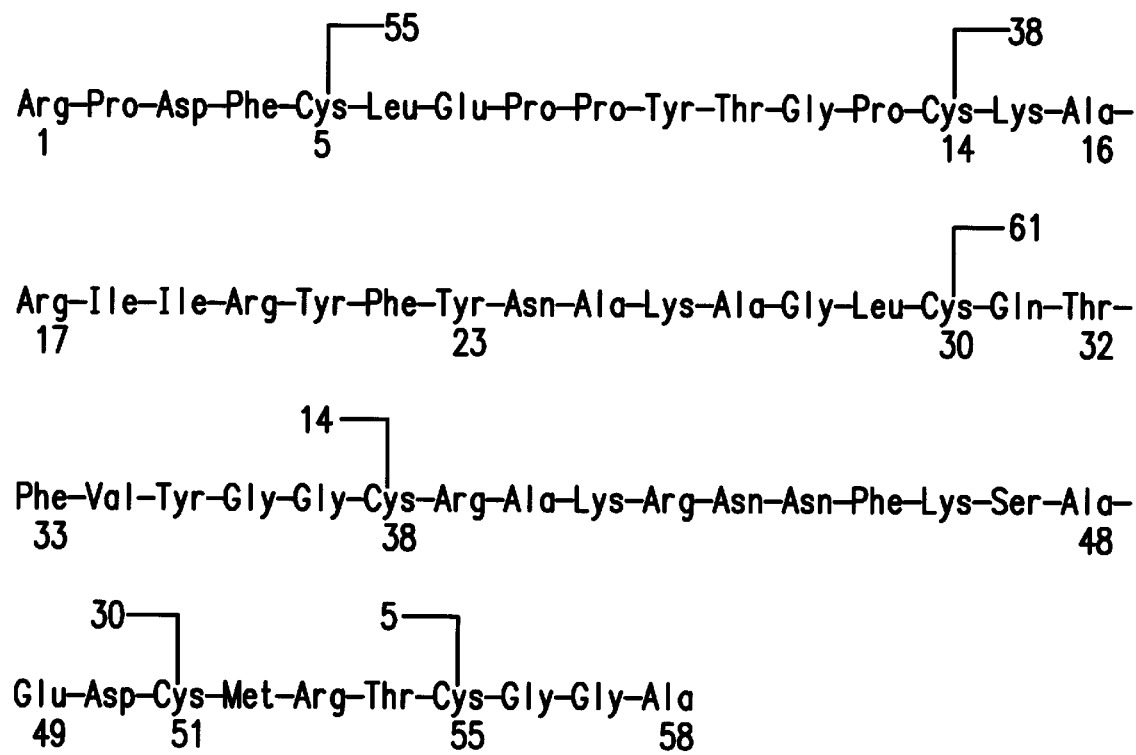
FIG. 10 shows (SEQ ID NO:2). the nucleic acid sequence encoding for aprotinin.

A series of constructs were prepared to direct the expression of the pharmaceutical protein aprotinin from the plastid. The nucleic acid sequence encoding for aprotinin (FIG. 10) was cloned into a plastid expression construct to control the expression of aprotinin from the T7 gene 10 leader promoter which is induced from a nuclearly expressed, plastid targeted T7 Polymerase. The constructs used in which the aprotinin sequence was cloned are as described in U.S. Pat. No. 5,576,198, the entirety of which is incorporated herein by reference. The plastid transformation vector pCGN6146 is designed by replacing the DNA sequence encoding for GUS from pCGN4276 (described in U.S. Pat. No. 5,576,198) with the coding sequence of aprotinin. The tobacco plastid transformation construct pCGN6147 contains the same elements as pCGN6146 except pCGN6147 contains the six 5' amino acids of the GUS encoding sequence ligated to the 5' terminus of the aprotinin encoding sequence. The six amino acids of the 5' terminus of the GUS nucleotide sequence are included to aid in the translation of the aprotinin protein. The tobacco plastid transformation vector pCGN6156 is essentially the same as pCGN4276 except the coding region of aprotinin is cloned to the 3' end of the GUS coding sequence Thus, pCGN6156 contains as operably linked the T7 promoter, a DNA sequence encoding for GUS fused with the DNA sequence encoding for aprotinin and the psbA 3' transcription termination sequence.

A plastid expression construct, pCGN6154, was constructed from pCGN4276 by replacing the GUS coding sequence with the aprotinin protein operably linked to the 3' terminus of the coding sequence of cytochrome $f$ (petA) of the tobacco chloroplast. Thus, pCGN6154 contains the T7 promoter sequence operably linked to the nucleotide sequence of petA and aprotinin. The petA sequence is included to direct the expressed aprotinin protein to the thylakoid.

Example 2 Plant Transformation

2A. Nuclear Transformation

Tobacco plants transformed to express the constructs pWRG4744 and pWRG4747 in the nucleus of a plant cell may be obtained as desribed by Horsch et al. (*Science* (1985) 227:1229–1232).

2B. Plastid Transformation

Tobacco plastids are transformed by particle gun delivery of microprojectiles as described by Svab and Maliga (*Proc. Natl. Acad. Sci.* (1993) 90:913–917), and described here.

Dark green, round leaves are cut, preferably from the middle of the shoots, from 3–6 week old *Nicotiana tabacum* cv. Havana which have been maintained in vitro on hormone free MS medium (Murashige and Skoog, (1962) *Physiol Plant.* 15, 473–497) supplemented with B5 vitamins in Phytatrays or sundae cups with a 16 hour photoperiod at 24° C. Each cut leaf is then placed adaxial side up on sterile filter paper over tobacco shoot regeneration medium (TSO medium: MS salts, 1 mg/l $N^6$-benzyladenine, 0.1 mg/l 1-naphthaleneacetic acid, 1 mg/l thiamine, 100 mg/l inositol, 7 g/l agar pH 5.8 and 30 g/l sucrose). Leaves are preferably placed in the center of the plate with as much contact with the medium as possible. The plates are preferably prepared immediately prior to use, but may be prepared up to a day before transformation by particle bombardment by wrapping in plastic bags and storing at 24° C. overnight.

Tungsten or gold particles are sterilized for use as microcarriers in bombardment experiments. Particles (50 mg) are sterilized with 1 ml of 100% ethanol, and stored at −20° C. or −80° C. Immediately prior to use, particles are sedimented by centrifugation, washed with 2 to 3 washes of 1 ml sterile deionised distilled water, vortexed and centrifuged between each wash. Washed particles are resuspended in 500 μl 50% glycerol.

Sterilized particles are coated with DNA for transformation. Twenty-five micoliter aliquots of sterilized particles are added to a 1.5 ml microfuge tube, and 5 μg of DNA of interest is added and mix by tapping. Thirty-five microliters of a freshly prepared solution of 1.8M $CaCl_2$ and 30 mM spermidine is added to the particle/DNA mixture, mixed gently, and incubated at room temperature for 20 minutes. The coated particles are sedimented by centrifuging briefly. The particles are washed twice by adding 200 μl 70% ethanol, mixing gently, and centifuging briefly. The coated particles are resuspended in 50 μl of 100% ethanol and mixed gently. Five to ten microliters of coated particles are used for each bombardment.

Transformation by particle bombardment is carried out using the PDS 1000 Helium gun (Bio Rad, Richmond, Calif.) using a modified protocol described by the manufacturer.

Plates containing the leaf samples are placed on the second shelf from the bottom of the vacuum chamber and bombarded using the 1100 p.s.i. rupture disk. After bombardment, petriplates containing the leaf samples are wrapped in plastic bags and incubated at 24° C. for 48 hours.

After incubation, bombarded leaves are cut into approximately 0.5 $cm^2$ pieces and placed abaxial side up on TSO medium supplemented with 500 μg/ml spectinomycin. After 3 to 4 weeks on the selection medium, small, green spectinomycin resistant shoots will appear on the leaf tissue. These shoots will continue to grow on spectinomycin containing medium and are referred to as primary putative transformants.

When the primary putative transformants have developed 2 to 3 leaves, 2 small pieces (approximately 0.5 $cm^2$) are cut from each leaf and used for either selection or for a second round of shoot regeneration. One piece is placed abaxial side up on plates containing TSO medium supplemented with 500 μg/ml spectinomycin, and the other piece is placed abaxial side up on TSO medium supplemented with 500 μg/ml each of spectinomycin and streptomycin. Positive transformants are identified as the shoots which form green callus on the TSO medium containing spectinomycin and streptomycin.

After 3 to 4 weeks, the tissue placed on TSO medium containing only spectinomycin, which has been identified as positive on the TSO medium with spectinomycin and streptomycin, will develop green shoots. Two to four shoots of each positive transformant are selected and transferred to TSO medium supplemented with 500 μg/ml spectinomycin for generation of roots. Southern analysis is performed on 2 shoots to confirm homoplasmy as described below. Shoots from homoplasmic events are transferred to the greenhouse for seed production, while transformants which are not homoplasmic are sent through a second round or regeneration on TSO medium with 500 μg/ml spectinomycin to attain homoplasmy.

Example 3 Analysis of Transplastomic Tobacco Plants Transformed with Herbicide Tolerance Constructs 3A. Southern Analysis Transformed plants selected for marker aadA marker gene expression are analyzed to determine whether the entire plastid content of the plant has been transformed (homoplastic transformants). Typically, following two rounds of shoot formation and spectinomycin selection, approximately 50% of the transgenic plantlets which are analyzed are homoplastic, as determined by Southern blot analysis of plastid DNA. Homoplasmic plantlets are selected for further cultivation.

Genomic DNA is isolated from transformed tobacco plants, electrophoresed, and transferred to filters as described in Svab et al. ((1993), *Proc Natl Acad Sci*, 90:913–917).

Homoplasmic tobacco plants transformed to express CP4 EPSPS in plastids were identified using a probe prepared from a 2.4 kb EcoRI/EcoRV fragment from the vector pOVZ2 (similar to poVZ15 described in Zoubenko, et al. 1994, supra). The 2.4 kb probe fragment encompasses part of the targeting sequence.

Results of the Southern hybridizations identified 3 homoplasmic lines from tobacco transformed with the constructs pMON30123 and pMON30130 and 1 line from tobacco transformed with pMON38773 for further analysis.

The complete disappearance of the 3.27 Kb native tobacco BamHI fragment in the lines 30123-19-1A, 30123-23-2A, 30123-18-1B, 30130-51-2A, 30130-51-2P, 30130-57-1P, and 38773-6 with a probe covering the region of integration, and the appearance of expected sized bands for the inserted DNA fragments in those transformants, 5.14 kb and 0.9 kb, establishes that the transformed plants are homoplasmic for the intended constructs.

Results of the Southern hybridizations identified 3 homoplasmic lines from tobacco transformed with pCGN5177, lines 74-1B-P, 74-2 and 74-7.

Transplastomic 5175 and 6114 tobacco lines were analyzed by Southern hybridization for homoplasmy as described above. Results of the Southern hybridizations identified 4 homoplasmic lines from tobacco transformed with pCGN6114.

Results from hybridizations of 5175 transplastomic tobacco lines identified one line, 76-4A-F, as homoplasmic, and a second line as 95% homoplasmic.

Homoplasmic tobacco plants transformed to express BXN/AHAS in plastids were identified using Southern hybridizations as described above.

Results of the Southern hybridizations identified 14 homoplasmic lines from tobacco transformed with pCGN5026. The filters were reprobed with a BXN gene fragment, and 21 lines were found to contain BXN, 14 lines of which were homoplasmic.

3B. Northern Analysis

In order to determine the level of transcription of the EPSPS, BXN or AHAS mRNA expressed in the transplastomic tobacco plants, Northern blot hybridizations were performed with total RNA isolated from each of the lines identified. Total RNA was isolated using TRIzol reagent (Gibco-BRL Life Technologies, Gaithersburg, Md.) according to the manufacturers protocol. Total RNA, 2 μg, was separated on a denaturing agarose gel and transferred to nylon membrane (Maniatis et al., 1989, supra). Radioactive probes for hybridizations were prepared using random primer labeled (using Random Primer labeling kit from Boehringer Mannheim) CP4 EPSPS, phytoene desaturase, BXN, or AHAS fragments and hybridizations were carried out in 2×SSPE (Maniatis, et al. , 1989, supra) , at 60° C. Filters were stripped and reprobed with a plastid 16S ribosomal RNA gene probe (from pPRV112A, Zoubenko, et al., 1994, supra) to confirm homogenous loading of RNA on the filter.

Results of the Northern hybridizations performed with EPSPS probes demonstrate that all seven (7) lines examined express CP4 EPSPS mRNA. Hybridizations performed with the 16S ribosome probe confirm that denaturing gels were loaded with similar amounts of total RNA for each sample. Furthermore, transplastomic tobacco lines expressing EPSPS from the Prrn/rbcL(RBS) (pMON30123) regulatory elements express EPSPS mRNA to higher levels than tobacco plants homoplasmic for EPSPS controlled by the Prrn/G10L (pMON38773) promoter/RBS sequences.

Results of Northern hybridizations performed with with BXN, AHAS and crtI probes demonstrates that all homoplasmic 5026, 5175, and 5177 tobacco lines expressed crtI, BXN and/or AHAS mRNA.

3C. Western Blot Analysis of Tobacco CP4 EPSPS

To determine the expression of the EPSPS Western blot analysis was performed on a single line from each construct, pMON30123, pMON30130, and pMON38773.

Total soluble protein was extracted from frozen leaf tissue by grinding 250 mg tissue in 250 μl of PBS buffer (1 mM $KH_2PO_4$, $Na_2HPO_4$, 0.137M NaCl, 2.7 mM KCl pH 7.0) containing protease inhibitors. The homogenate is centrifuged for 5 minutes, and the supernatant is transferred to a fresh tube. The concentration of the protein in the supernatant is determined using a protein concentration assay (BioRad, Richmond, Calif.).

Extracted total protein is electrophoresed on a 4–20% SDS-PAGE gel (Sigma, St Louis, Mo.), and transferred to PVDF membrane in 1×SDS-PAGE buffer (Maniatis et al. 1989, Cold Spring Harbor Press). Standards of quantitated purified CP4 EPSPS protein were used to quantify the expression of the CP4 EPSPS as expressed in the plant plastid.

Western hybridizations are performed as described in Staub and Maliga (1993) *EMBO Journal*, 12(2) 601–606, except using antibodies raised to EPSPS. PVDF membranes containing the transferred electrophoresed protein were incubated in a blocking solution of PBS buffer containing 0.05% Tween-20 (PBS-T) and 5% milk overnight at 4° C. The membranes are then incubated in a solution of PBS-T containing 1% milk and a primary antibody raised in goats to the CP4 EPSPS for 2 hours at room temperature. The membranes are washed three times in a solution of PBS-T containing 0.1% milk, each wash for 5 minutes at room temperature. The membranes are then incubated in a solution of PBS-T containing 1% milk and sheep anti-goat antibody for 1 hour at room temperature, and washed again in PBS-T containing 0.1% milk, three times for 10 minutes at room temperature. A final wash using only PBS-T is performed before developing the membranes using a non-radioactive detection kit (ECL, Amersham).

TABLE 2

| Construct Number | Event Number | % Total Soluble Protein |
| --- | --- | --- |
| pMON30123 | T18-23-2A | 0.001 |
| pMON30130 | T18-51-2P | 0.002 |
| pMON38773 | 9706-6-1 | 0.2 |

The results listed in Table 2 demonstrate that significant increases in the level of EPSPS protein may be obtained from plants transformed to express EPSPS from the Prrn/G10L promoter. These results demonstrate that EPSPS expression driven by the Prrn/rbcLRBS regulatory sequences may produce approximately 0.001% of the total soluble protein as EPSPS, while in plants expressing EPSPS from the Prrn/G10L regulatory sequences express 0.2% of the total soluble protein as EPSPS. Subsequent lines have demonstrated total soluble protein of about 1% EPSPS when expressed from the Prrn/G10L regulatory sequences. These results, taken together with the results of the Northern hybridizations above, indicate that more efficient translation may be obtained from the G10L ribosome binding site.

Western immunoblot hybridization were also performed on 2 homoplasmic 5026 tobacco lines as described above, using antibodies raised against bromoxynil. The results of Western immunoblot analysis of total soluble protein extracted from tobacco lines transformed with pCGN5026 demonstrated that both homoplasmic lines produced nitrilase protein.

Western immunoblot analysis was performed as described above from total protein extracted from tobacco lines transformed with pCGN6114 and pCGN5197.

The results of the analysis demonstrated that bromoxynil was produced in 6114 tobacco lines ranging from 1% to 2% of the total soluble leaf protein.

The results of the Wetsrern analysis of the 20 5197 tobacco lines demonstrated that bromoxynil and Bt were both produced as 1% of the total soluble leaf protein.

3D. Analysis of EPSPS Enzyme Activity

The EPSPS enzyme activity in transplastomic tobacco plants containing the plastid expression vector pMON38773 was determined using a high pressure liquid chromatography (HPLC) assay.

Methods for the analysis of EPSPS enzyme activity are described in Padgette et al. (*J. Biol. Chem.* (1988) 263:1798–1802 and *Arch. Biochem. Biophys.* (1987) 258:7564–573) and Wibbenmeyer et al. (*Biochem. Biophys. Res. Commun.* (1988)153:760–766).

The results are summarized in Table 3 below.

TABLE 3

| Nuclear Enzymatic Activity Range | Nuclear % Total Plants In Range | Chloroplast 38773-6 |
|---|---|---|
| 1–3.7 μmol/mg | 1% | |
| >0.1 μmol/mg | 16% | |
| >10 nmol/mg | 55% | 16.39 nmol/mg |
| >1 nmol/mg | 32% | |
| 0 nmol/mg | 3% | |

These results demonstrate that EPSPS expression in plastids produces active EPSPS enzyme.

3E. Analysis for Glyphosate Tolerance

A transplastomic tobacco line homoplasmic for the construct pMON38773 was tested in vitro to determine the highest level of glyphosate tolerance. Explant tissue was prepared from leaf pieces of nontransgenic wild type tobacco control, Havanna, plants and the homoplasmic tobacco line 38773-6 and cultured for regeneration of shoots on TSO medium scribed above) supplemented with glyphosate levels of 50 μM, 75 μM, 100 μM, 150 μM and 200 μM. The results are summarized in Table 4 below. The number of explants producing shoots was determined at 3 weeks and 6 weeks after explant preparation and culturing on glyphosate containing medium.

TABLE 4

| Glyphosate Level (μM) | Total Number Explants | Number Regenerating 3 Weeks | Number Regenerating 6 Weeks | % Explant Regeneration |
|---|---|---|---|---|
| Wild Type | | | | |
| 50 | 10 | 0 | 0 | 0 |
| 75 | 10 | 0 | 0 | 0 |
| 100 | 10 | 0 | 0 | 0 |
| 150 | 10 | 0 | 0 | 0 |
| 200 | 10 | 0 | 0 | 0 |
| 38773-6 | | | | |
| 50 | 8 | 5 | 8 | 100 |
| 75 | 18 | 14 | 18 | 100 |
| 100 | 17 | 12 | 15 | 88 |
| 150 | 18 | 10 | 16 | 89 |
| 200 | 16 | 8 | 15 | 86 |

The above results demonstrate that at all levels of glyphosate examined, shoots regenerated from explants prepared from a tobacco line homoplasmic for pMON38773, while no shoots regenerated from explants prepared from nontransformed control plants. These results suggest that tobacco plants expressing EPSPS in plastids demonstrate tolerance to glyphosate levels of at least 200 μM.

Additional transplastomic lines were tested in vitro for glyphosate tolerance as described above. The results are shown in Table 5

TABLE 5

Summary of tobacco plastid transformation experiments with various constructs containing EPSPS genes.

| Construct | Spec/strep (+) | No. of shoots Gly 50 uM (+) |
|---|---|---|
| pMON38766 (Wild) | 1 | 0 |
| pMON38766 (T7) | 6 | 0 |
| pMON38773 (Wild) | 9 | 5 (1) |

TABLE 5-continued

Summary of tobacco plastid transformation experiments with various constructs containing EPSPS genes.

| Construct | Spec/strep (+) | No. of shoots Gly 50 uM (+) |
|---|---|---|
| pMON38797 (Wild) | 2 | 0 |
| pMON38798 | 6 | 6 |
| pMON38793 | 8 | 0 |
| pMON38796 | 4 | 0 |
| pMON45201 | 9 | 3 |
| pMON45204 | 12 | * |

(No. of shoots positive at 1 mM glyphosate)

These results demonstrate that these transplastomic lines show tolerance to glyphosate. The numbers in parentheses are the number of shoots resistant to selection at 1 mM glyphosate. Thus, as can be seen in table 5, tobacco lines are generated that are tolerant of selection at 1 mM glyphosate.

Homoplasmic tobacco plants of the line 38773-6 are sprayed with glyphosate using a track sprayer at concentrations corresponding to 0 oz/acre, 16 oz/acre, 32 oz/acre and 64 oz/acre to test for whole plant tolerance. Plant height was measured before and after spraying with glyphosate. The vegetative injury data was collected two weeks after spraying, while the reproductive injury data was collected at plant maturity.

Intial results indicate that homoplasmic tobacco lines sprayed are tolerant of glyphosate at the concentration of 16 oz/acre as demonstrated in the vegetative tissue injury (Table 6). As can be seen in Table 5 transplastomic lines were generated which demonstrated a good level of glyphosate tolerance at 32 oz/Acre. In subsequent experiments with additional transformed lines, transplastomic lines have shown tolerance to glyphosate at a level of 64 oz/Acre.

Tolerance is characterized by the continued growth and greening of tissues sprayed with glyphosate. However, as the concentration of glyphosate applied increased, there was a corresponding increase in the level of vegetative injury. In contrast, nontransformed control plants which were highly susceptible to glyphosate concentratioins as low as 16 oz/Acre.

TABLE 6

| Plant No. | Construct | Roundup rate (oz/A) | Plant height (cm) before spray (3/19/98) | Plant height (cm) after spray (4/3/98) | Vegetative injury (4/6/98) | Fertility rating (6/12/98) |
|---|---|---|---|---|---|---|
| 1 | 38773 | 0 | 12.2 | 30.5 | 0 | 0 |
| 2 | 38773 | 0 | 13.6 | 34.0 | 0 | 0 |
| 3 | 38773 | 0 | 8.6 | 23.8 | 0 | 0 |
| 4 | 38773 | 0 | 8.6 | 26.2 | 0 | 0 |
| 5 | 38773 | 0 | 7.8 | 28.8 | 0 | 0 |
| 6 | 38773 | 0 | 12.8 | 31.5 | 0 | 0 |
| 7 | 38773 | 0 | 12.2 | 31.6 | 0 | 0 |
| 8 | 38773 | 0 | 11.6 | 35.5 | 0 | 0 |
| 9 | 38773 | 16 | 9.0 | 29.0 | 1 | 0 |
| 10 | 38773 | 16 | 14.4 | 31.0 | 0 | 0 |
| 11 | 38773 | 16 | 13.4 | 32.0 | 0 | 0 |
| 12 | 38773 | 16 | 13.2 | 30.0 | 0 | 0 |
| 13 | 38773 | 16 | 14.2 | 30.5 | 0 | 1 |
| 14 | 38773 | 16 | 14.0 | 33.0 | 0 | 0 |
| 15 | 38773 | 16 | 13.2 | 30.2 | 0 | 0 |
| 16 | 38773 | 16 | 14.9 | 30.4 | 0 | 0 |
| 17 | 38773 | 32 | 12.0 | 26.5 | 2 | 4 |
| 18 | 38773 | 32 | 11.6 | 25.4 | 1 | 1 |
| 19 | 38773 | 32 | 9.4 | 22.0 | 1 | 3 |

TABLE 6-continued

| Plant No. | Con-struct | Roundup rate (oz/A) | Plant height (cm) before spray (3/19/98) | Plant height (cm) after spray (4/3/98) | Vege-tative injury (4/6/98) | Fertility rating (6/12/98) |
|---|---|---|---|---|---|---|
| 20 | 38773 | 32 | 11.2 | 23.0 | 2 | 4 |
| 21 | 38773 | 32 | 13.8 | 25.8 | 1 | 2 |
| 22 | 38773 | 32 | 12.4 | 23.0 | 1 | 4 |
| 23 | 38773 | 32 | 10.2 | 19.0 | 2 | 4 |
| 24 | 38773 | 32 | 13.8 | 23.2 | 2 | 3 |
| 26 | 38773 | 64 | 11.8 | 20.0 | 2 | 5 |
| 27 | 38773 | 64 | 13.0 | 22.0 | 2 | 5 |
| 28 | 38773 | 64 | 12.2 | 18.0 | 3 | 5 |
| 29 | 38773 | 64 | 15.8 | 23.0 | 2 | 5 |
| 30 | 38773 | 64 | 10.4 | 17.5 | 2 | 5 |
| 32 | 38773 | 64 | 15.0 | 18.5 | 2 | 5 |
| 33 | 38773 | 64 | 13.8 | 21.8 | 2 | 5 |
| 34 | 38773 | 64 | 13.6 | 19.0 | 3 | 5 |
| 35 | 38773 | 64 | 10.8 | 16.0 | 3 | 5 |
| 36 | Wild type | 0 | 21.0 | 40.6 | 0 | 0 |
| 37 | Wild type | 0 | 16.0 | 38.0 | 0 | 0 |
| 38 | Wild type | 0 | 15.0 | 34.6 | 0 | 0 |
| 39 | Wild type | 0 | 17.6 | 32.2 | 0 | 0 |
| 40 | Wild type | 0 | 15.0 | 31.6 | 0 | 0 |
| 41 | Wild type | 0 | 14.0 | 32.0 | 0 | 0 |
| 42 | Wild type | 16 | 10.0 | 11.8 | 3 | 5 |
| 43 | Wild type | 16 | 8.0 | 10.0 | 3 | 5 |
| 44 | Wild type | 16 | 8.6 | 11.0 | 3 | 5 |
| 45 | Wild type | 16 | 8.0 | 14.0 | 3 | 5 |
| 46 | Wild type | 16 | 9.8 | 11.0 | 3 | 5 |
| 47 | Wild type | 16 | 10.4 | 14.0 | 3 | 5 |
| 48 | Wild type | 32 | 10.8 | 13.2 | 3 | 5 |
| 49 | Wild type | 32 | 9.0 | 13.0 | 3 | 5 |
| 50 | Wild type | 32 | 8.0 | 10.2 | 3 | 5 |
| 51 | Wild type | 32 | 11.0 | 14.0 | 4 | 5 |
| 52 | Wild type | 32 | 9.8 | 13.0 | 3 | 5 |
| 53 | Wild type | 32 | 8.0 | 10.8 | 4 | 5 |
| 54 | Wild type | 64 | 7.5 | 8.6 | 4 | 5 |
| 55 | Wild type | 64 | 11.2 | 12.5 | 4 | 5 |
| 56 | Wild type | 64 | 10.2 | 12.8 | 4 | 5 |
| 57 | Wild type | 64 | 11.5 | 13.0 | 4 | 5 |
| 58 | Wild type | 64 | 13.0 | 15.0 | 4 | 5 |
| 59 | Wild type | 64 | 9.8 | 11.2 | 4 | 5 |

Vegetative injuries:
0 = normal plant
1 = slight chlorosis of new leaves and stunting
2 = severe chlorosis of new leaves, malformation of new leaves, and severe stunting
3 = dying plant
4 = dead plant
Fertility ratings:
0 = Fertile, no delay in maturity, lots of seed
1 = Some abortion, slight delay in seed set, seed
2 = Significant abortion, significant delay in seed set, some seed
3 = Very severe abortion, immature seed pots, a few seed
4 = malformed flowers; if flowered, extreme delay in flowering and no seed produced
5 = dead plant 3F. BT/BXN Analysis Homoplasmic tobacco plants of the lines 5175 and 5197 are sprayed with Buctril herbicide at a concentration of 4% to test for whole plant tolerance.

Results of the spray test with Buctril demonstrated that all 5197 lines expressing bxn were completely resistant when sprayed with a solution containing 4% Buctril herbicide.

Two lines out of six 5175 lines tested were completely resistant to the herbicide when sprayed with a 4% solution containing Buctril.

3G. Norflurazon Resistance Analysis

An experiment was set up to determine the efficacy of the Crt I trait with respect to resistance to the herbicide Norflurazon. Three 5177 transformed lines, 74-1B-P, 74-2-A, and 74-7-C and three control lines were planted. Plants were grown for seven weeks and then watered with a 3 $\mu$M Norflurazon solution. Plants negative for the presence of the crtI plastid-borne gene were bleached by Norflurazon trearment, positive plants stayed green and continued to grow.

The results show that the three homoplasmic 5177 tobacco lines were resistant to the 3 $\mu$M Norflurazon solution, while the control plants were all susceptible to the solution (Table 7).

TABLE 7

| Line | Control/Transgenic | Result |
|---|---|---|
| Xanthi | Control | Susceptible |
| 2560A Xanthi | Control | Susceptible |
| 75-5D-A | Control | Susceptible |
| 74-1B-P | homoplasmic | Resistant |
| 74-2-A | homoplasmic | Resistant |
| 74-7-C | homoplasmic | Resistant |

Example 4 Analysis of hGH Transgenic Tobacco Plants

4A. Southern Analysis

Transformed plants selected for aadA marker gene expression are analyzed to determine whether the entire plastid content of the plant has been transformed (homoplastic transformants). Homplasmic plants are selected using Southern hybridization for further cultivation.

Genomic DNA is isolated from transformed tobacco plants, electrophoresed, and transferred to filters as described in Svab et al. ((1993), *Proc Natl Acad Sci*,. 90:913–917).

Homoplasmic tobacco plants transformed to express hGH were identified using a probe prepared from a 2.4 kb EcoRI/EcoRV fragment from the vector pOVZ2 (similar to pOVZ15 described in Zoubenko, et al. 1994, supra) . The 2.4 kb probe fragment encompasses part of the targeting sequence.

The complete disappearance of the 3.27 Kb native tobacco BamHI fragment in the lines with a probe covering the region of integration, and the appearance of the expected size band for the inserted DNA fragments in those transformants, 5.6 kb, establishes that the transformed plants are homoplasmic for the intended constructs.

4B. Protein Expression Analysis

Homoplasmic tobacco lines expressing hGH and nuclear tobacco transformants are used to determine the expression of the hGH protein. Western blot analysis was performed on tobacco lines containing constructs pWRG4838, pMON38755 and pMON38794 for plastid expression and an ELISA assay was used for transgenic tobacco lines containing pWRG4744 and pWRG4747 for nuclear expression of hGH.

Total protein extractions and western blot procedures were performed as described above, with the exception of the primary antibody was raised against hGH.

TABLE 8

Expression Levels of hGH in Tobacco Nuclear Genome and Plastid genome

| Construct | Expression | Expression Level % Total Soluble Protein |
| --- | --- | --- |
| pWRG4744 | nuclear | 0.002–0.125% |
| pWRG4747 | nuclear | 0.002–0.025% |
| pWRG4838 | plastid | 0.2% |
| pMON38755 | plastid | 1.0% |
| pMON38794 | plastid | 7.0% |

Results of the Western analysis (Table 8) demonstrates that hGH expressed in plastids of plant cells accumulates to significantly higher levels than hGH expressed in the nucleus and targeted to either the cytoplasm or plastid of plant cells. Tobacco plants transformed to express hGH in the nucleus accumulated hGH levels of 0.002% (cytoplasmic targeted) to 0.025% (plastid targeted) of total soluble leaf protein, while tobacco plants expressing hGH in the plastid accumulated hGH levels of 0.2% to 7.0% of the total soluble leaf protein as hGH. Furthermore, homoplasmic tobacco plants expressing hGH directed from the Prrn/G10L regulatory sequences accumulate 35 fold higher levels of hGH than homoplasmic tobacco plants expressing hGH directed from the PpsbA promoter sequence.

4C. Characterization of hGH Protein Expressed in the Plastid

In order to determine whether the hGH expressed from plastids was properly processed, experiments were performed to determine correct folding and bioacitivity.

Two bottom leaves of transplastomic tobacco lines containing pMON38794 were used to extract and purify hGH. Large veins were removed from the excised leaves, and the leaf tissue was cut into small sections (approximately 0.5 cm$^2$). The leaf pieces were flash frozen in liquid nitrogen and ground to a fine powder in a chilled mortar and pestle. Ten grams of frozen, ground leaf tissue was added to ice cold 100 mM Tris base solution (30 ml) and mixed vigorously by vortexing for 5 minutes. The solution was filtered through a single layer of cheese cloth.

From the filtered solution, three separate samples were prepared. The first sample was prepared by cetrifuging 4 ml of the filtrate for 1 minute at 16,000 rpm. The centrifugate was aliquoted into 1 ml vials and frozen in dry ice. The remaining filtrate was centrifuged for 10 minutes at 4800 rpm, and several 0.5 ml aliquots were frozen as above for the second sample. To the remaining centrifuged filtrate (approximately 25 ml), 200 µl of glacial acetic acid was added to lower the pH from 8.2 µl to 4.56. The solution was centrifuged at 4800 rpm for 30 minutes, and the supernatant was frozen over dry ice for the third sample.

Total soluble protein (TSP, Table 9) was calculated in these samples by standard protein assay procedures (Maniatis,), and the percent purity of hGH was calculated based on results from Western blot analysis using known concentrations of starting material.

TABLE 9

| Sample ID | TSP mg/mL | GP2000 mg/L | % Purity |
| --- | --- | --- | --- |
| Filtered Extract immediately centrifuged and frozen | 6.3 | 28 | 0.45% |
| Filtered extract centrifuged at 4800 rpm for 10 min and frozen | 6.4 | 28 | 0.45 |
| pH adjusted and centrifuged extract | 0.75 | 21 | 2.8% |

The pH adjusted and centrifuged extract was purified by Reverse Phase-HPLC (RP-HPLC) for electrospray mass spectrometry and amino-terminal amino acid sequencing. RP-HPLC was performed using a Perkin-Elmer series 200 pump and autosampler and a Vydac C8 (250 by 4.6 mm) RP-HPLC column. 750 microliters of sample was loaded onto the column equilibrated with 20 mM trifluoroacetic acid (TFA) and 50% acetonitrile. After loading, the column was washed for 2 minutes with 50% acetonitrile, 20 mM TFA followed by a 2% linear acetonitrile gradient over 10 minutes followed by a 10% acetonitrile gradient over 1 minute. The flow rate was a constant 1.5 ml/minute with the column eluate monitored at 278 nm with a Perkin-Elmer 785 detector. Data was collected and analyzed with a PE-Nelson Turbochrom data system.

Figure 11:
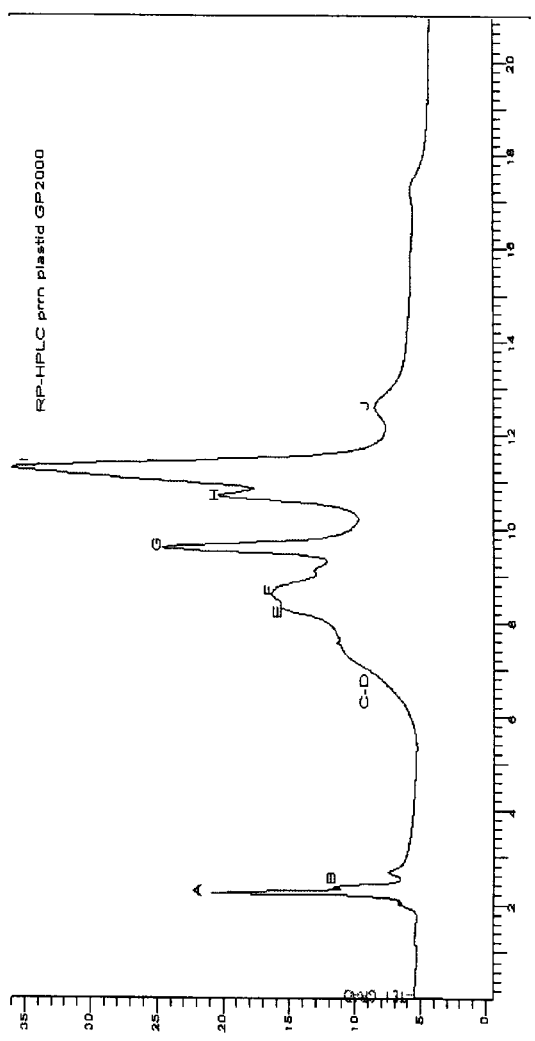
FIG. 11 shows the results of the RP-HPLC analysis for example 4B.

The results of the RP-HPLC analysis are shown in FIG. 11. Peak I (tallest peak) has the retention time expected for properly folded, native 22 kDa GP2000. This peak was collected and dried down in a Savant Speed-Vac for amino terminal sequencing and electrospray mass spectrometry.

Electrospray ionization mass spectrometry (MS) analysis used a Micromass Q-Tof electrospray time-of-flight mass spectrometer. The samples were prepared by resuspending in 50% methanol+2% acetic acid, and infused into the source of the mass spectrometer at a rate of 4 mL/min. The raw data shown in FIG. 12 shows a series of ions corresponding to the specie(s) present in the sample with varying numbers of protons attached. The axes of this spectrum are intensity versus mass-to-charge ratio of the specie(s) present. A deconvolution algorithm is used to convert this series of multiply charged ions into a molecular weight spectrum.

The results of the mass spectrometry of the RP-HPLC peak I shows 4 major protein species of different molecular mass. The 21,997 kDa species represents the predicted mass of hGH with the predicted N-terminal Phe removed by over-cleavage of the Ubiquitin protease. The 22,124 kDA species represents the predicted mass of properly processed, correct amino acid sequence of hGH. The 22,507 kDA and 22,664 kDA species are thought to represent an hGH with the N-terminal Phe and hGH which have been modified during plant extraction procedures, respectively. The calculated molecular mass of the proteins suggests that the hGH expressed from the plastid is properly folded (i.e. the correct disulfide bonds are created).

Amino terminal sequencing was done by standard Edman degradation, and confirmed the N-terminal sequences discussed above.

4D. Bioactivity of hGH Expressed in Plant Plastids

Bioactivity of the pH adjusted and centrifuged extract was tested using cells from an Nb2 cell line. These cells proliferate in the presence of growth hormone and other estrogenic type compounds. The assay involves putting various concentrations of growth hormone-containing extract into a 96 well plate. Then a constant amount of cells are added to each well. The plate is incubated for 48 hrs and then a reagent called MTS is added. Metabolizing cells take up the MTS and convert it to a blue colored substance. The more cells there are the more blue color in the well. The blue color is measured using a spectrophotometer. The number of cells should be proportional to the concentration of growth hormone in the media. At some high concentration one expects that the cells will become saturated with growth hormone and that the dose response will level off. At very low hGH concentrations essentially no enhanced growth is seen. A sigmoidal shape grapf is expected to be produced graphing the cell number (or absorbance) vs hGH concentration graph.

Figure 13:
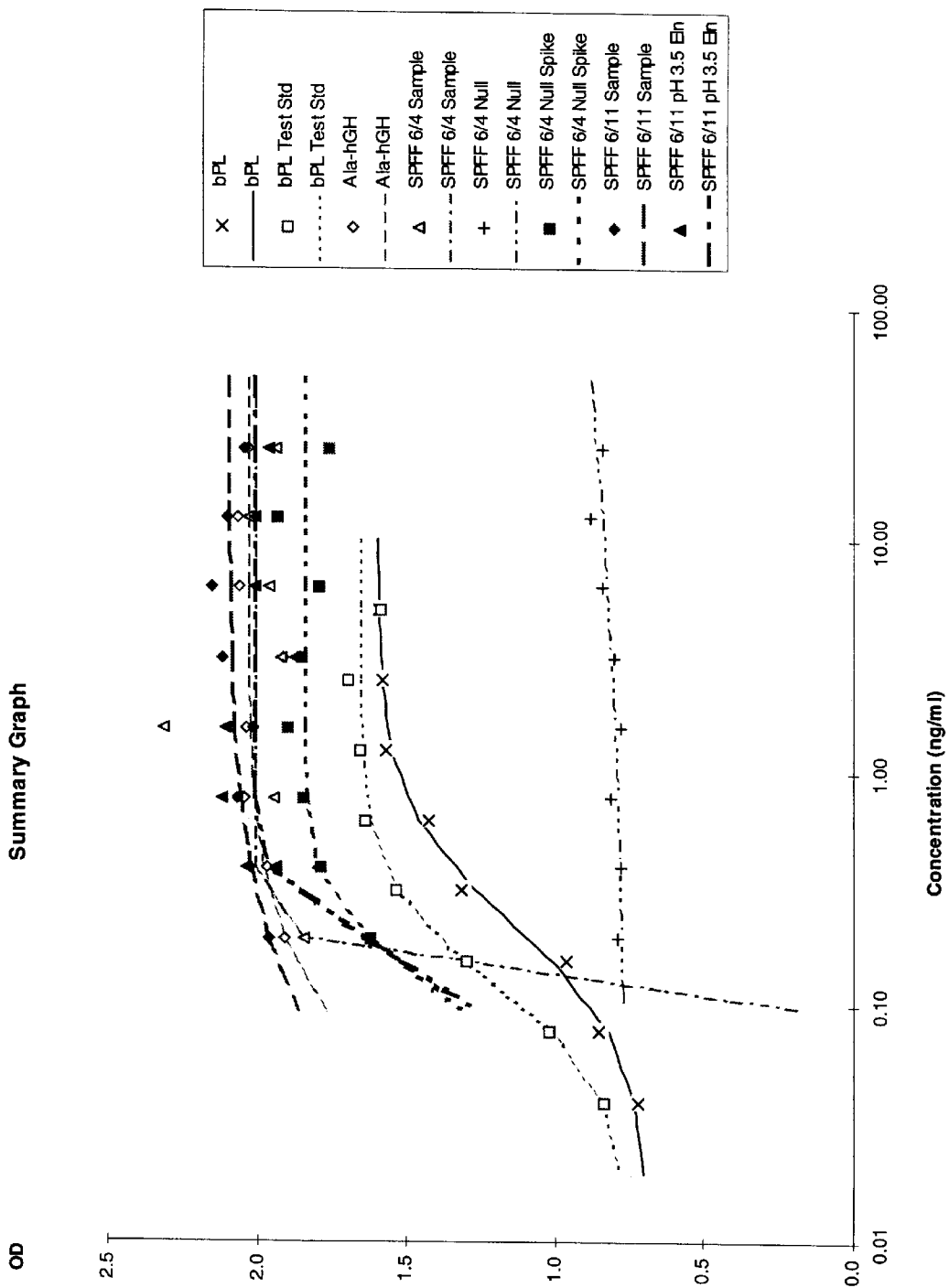
FIG. 13 shows a graphic representation of the bioactivity of hGH expressed from a plant plastid. The samples represented on the graph are a bovine prolactin (bPL), an hGH expressed from *E. coli* (Ala-hGH), and a null transgenic spiked with bovine prolactin (SPFF Null Spike) as positive controls, a null transgenic (SPFF Null) as a negative control, and transgenic samples from a sepharose column (SPFF Sample, SPFF Sample) and a transgenic sample eluted from the sepharose column at pH3.5 (SPFF pH3.5 Eln).

The results of the bioactivity assay (FIG. 13) demonstrates that the hGH expressed from a plant plastid has a sigmoidal shape when graphed as absorbance vs hGH concentratioin.

Example 5 Analysis of Aprotinin Transplastomic Tobacco Plants

5A. Western Analysis of Aprotinin Expression in Plastids

Homoplasmic tobacco lines expressing are used to determine the expression of the aprotinin protein Western blot analysis was performed on tobacco lines containing constructs pCGN6146, pCGN6147, pCGN6154 and pCGN6156 for plastid expression of aprotinin.

Total protein extractions and western blot procedures were performed as described above, with the exception of the primary antibody was raised against aprotinin.

The results of the Western analysis indicate that aprotinin is expressed from the T7 polymerase promoter when the aprotinin coding sequence is fused with either the PetA or full length GUS gene. Furthermore, these results indicate that the petA sequence efficiently targets the aprotinin protein to the plant cell thylakoid.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method for increasing the production of a protein in a plant cell containing plastids, wherein said method comprises:

transforming plastids of said plant cell with a construct comprising the following as operably joined components in the 5' to 3' direction of transcription
   a) a promoter functional in a plant plastid;
   b) a DNA sequence encoding a peptide that confers tolerance to the herbicide glyphosate;
   c) a transcription termination region; and
   d) a ribosome binding site from the T7 bacteriophage gene 10 joined to said promoter component; and growing plant cells comprising said transformed plastids under conditions wherein said DNA sequence is transcribed in said plastid.

2. The method according to claim 1 wherein said DNA sequence encodes a glyphosate-tolerant 5-enolpyruvylshikimate-3-phosphate synthase.

3. The method according to claim 2 wherein said DNA sequence is selected from the group consisting of the *E. coli* or Salmonella aroA gene, the Agrobacterium CP4 gene, mutant petunia EPSPS gene, mutant EPSPS gene of Psuedomonas strain LBAA and the *Bacillus subtilis* aroE gene.

4. The method according to claim 1 wherein said DNA sequence encodes a glyphosate-modifying enzyme.

5. The method according to claim 4 wherein said glyphosate-modifying enzyme is encoded by a gene selected from the group consisting of the gox, hph, glpA and glpB genes.

6. A plant cell produced according to the method of claim 1 comprising about 1% or more of total soluble protein as a protein expressed from a herbicide-tolerance gene.

7. A plant comprising a plant cell of claim 6 tolerant of the herbicide glyphosate when said herbicide is applied at a rate of at least about 16 ounces per acre.

8. A plant according to method of claim 7 tolerant of the herbicide glyphosate when said herbicide is applied at a rate of at least about 32 ounces per acre.

9. A plant according to method of claim 8 tolerant of the herbicide glyphosate when said herbicide is applied at a rate of 64 ounces or greater per acre.

10. A method according to claim 1 wherein selection for said herbicide tolerance is made on media containing glyphosate at a concentration from at least about 50 $\mu$M to about 200 $\mu$M.

11. A method according to claim 10 wherein selection for said herbicide tolerance is made on media containing glyphosate at a concentration from about 1 mM.

12. A plant cell produced according to the method of claim 1.

* * * * *